(12) United States Patent
Graupe et al.

(10) Patent No.: US 7,747,316 B2
(45) Date of Patent: Jun. 29, 2010

(54) BLIND ADAPTIVE FILTER EXTRACTION OF FETAL ELECTROCARDIOGRAM SIGNAL ESTIMATE

(75) Inventors: Daniel Graupe, Highland Park, IL (US); Menachem H. Graupe, Mequon, WI (US); Yunde Zhong, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 44 days.

(21) Appl. No.: 11/795,889

(22) PCT Filed: Jan. 27, 2006

(86) PCT No.: PCT/US2006/002981

§ 371 (c)(1),
(2), (4) Date: Jul. 24, 2007

(87) PCT Pub. No.: WO2006/081447

PCT Pub. Date: Aug. 3, 2006

(65) Prior Publication Data

US 2008/0125668 A1    May 29, 2008

(51) Int. Cl.
*A61B 5/0444* (2006.01)
(52) U.S. Cl. .................................. 600/511; 600/376
(58) Field of Classification Search ................. 600/376, 600/511
See application file for complete search history.

(56) References Cited

U.S. PATENT DOCUMENTS

2007/0066908 A1* 3/2007 Graupe et al. ............... 600/511

\* cited by examiner

*Primary Examiner*—Mark W Bockelman
*Assistant Examiner*—Eric D. Bertram
(74) *Attorney, Agent, or Firm*—Robert J. Brill; Brill IP Law Office

(57) ABSTRACT

A blind adaptive filter of an apparatus in an example employs a frequency domain ECG-feature vector and a time domain ECG feature vector with a maternal ECG parameter estimate and a set of candidate fetal ECG estimates that satisfy the frequency domain ECG-feature-vector, to extract a fetal ECG signal estimate from raw abdominal ECG signals of a pregnant female. The fetal ECG signal estimate satisfies the frequency domain ECG feature-vector and the time domain ECG feature vector.

20 Claims, 19 Drawing Sheets

BLIND ADAPTIVE FILTER EXTRACTION OF FETAL ELECTROCARDIOGRAM SIGNAL ESTIMATE

BACKGROUND

There are fundamental theoretical limitations on any conventional ICA-based (independent component analysis-based) or AMUSE-Based blind separation methods. These are due to their requirement that the number of observations (e.g., electrode pairs) must be less or equal to the number of uncorrelated signal sources.

In the fECG (fetal electrocardiogram) extraction, this is not the case. Each electrode has its own, at least partly uncorrelated noise, due to maternal abdominal myoelectric activity and other noises picked up by these electrodes and which differ per each abdominal electrode placement. Also, the mECG (maternal electrocardiogram) and fECG in each channel are partly uncorrelated. Hence, adding electrodes will increase the number of noise sources which are not negligible (amplitude-wise) in weeks 32 of gestation and earlier, thus preventing adequate noise filtering via ICA-based or AMUSE-based blind separation methods. Furthermore, the mECG is of many times (even hundreds) of times stronger that the fECG signal embedded in it and especially than the P or T components of the fECG. Finally, the various noises in which the fECG is embedded may also be stronger by a factor of ten or more (depending on gestation age) and more so with respect to its P or T components.

Whereas Doppler ultrasound methods allow detection of fetal heartbeat down to the 10th-12th gestation week, no ultrasound method can yield useful time recordings of fECG. However, access to reliable and easily extractable fECG recordings would help the physician to better determine fetal heart condition and in some cases, diagnose fetal cardiac defects early in the pregnancy. Hence, in some cases, these can be treated by medication administered to the mother.

SUMMARY

The invention in an implementation encompasses an apparatus. The apparatus comprises a blind adaptive filter that employs a frequency domain ECG-feature vector and a time domain ECG feature vector with a maternal ECG parameter estimate and a set of candidate fetal ECG estimates that satisfy the frequency domain ECG-feature-vector, to extract a fetal ECG signal estimate from raw abdominal ECG signals of a pregnant female. The fetal ECG signal estimate satisfies the frequency domain ECG feature-vector and the time domain ECG feature vector.

Another implementation of the invention encompasses a method. A fetal ECG signal estimate that satisfies a time domain vector is extracted through employment of a blind adaptive filter that employs the time domain vector with a maternal ECG parameter estimate and a set of candidate fetal ECG estimates that satisfy a frequency domain vector.

A further implementation of the invention encompasses a method. A signal that comprises maternal electrocardiogram information, fetal electrocardiogram information, and non-electrocardiogram noise is input into a first blind adaptive filter stage. A feature vector of basic frequency domain features that are common to electrocardiogram signals is employed at the first blind adaptive filter stage to generate a maternal electrocardiogram parameter estimate and a set of candidate fetal electrocardiogram estimates that satisfy the feature vector of basic frequency domain features. The maternal electrocardiogram parameter estimate and the set of candidate fetal electrocardiogram estimates are input into a second blind adaptive filter stage. A feature vector of basic time domain features that are common to electrocardiogram signals is employed at the second blind adaptive filter stage to extract an initial fetal electrocardiogram signal estimate that satisfies the feature vector of basic time domain features. One or more sets of selected time samples of the initial fetal electrocardiogram signal estimate are filtered to remove noise from the initial fetal electrocardiogram signal estimate to yield a final fetal electrocardiogram signal estimate.

DESCRIPTION OF THE DRAWINGS

Features of exemplary implementations of the invention will become apparent from the description, the claims, and the accompanying drawings in which:

DETAILED DESCRIPTION

Referring to the BACKGROUND section above, in contrast to ICA-based (independent component analysis-based) or AMUSE-Based blind signal separation (BSS) methods, an exemplary implementation is based on blind adaptive filtering (BAF) which requires only a single observation channel, namely, a single electrode pair to retrieve the desired signal. Hence, in case of several raw signal channels, namely, several electrode pairs (several observation channels), each extracted signal is derived using only one raw observation channel.

Figure 1:
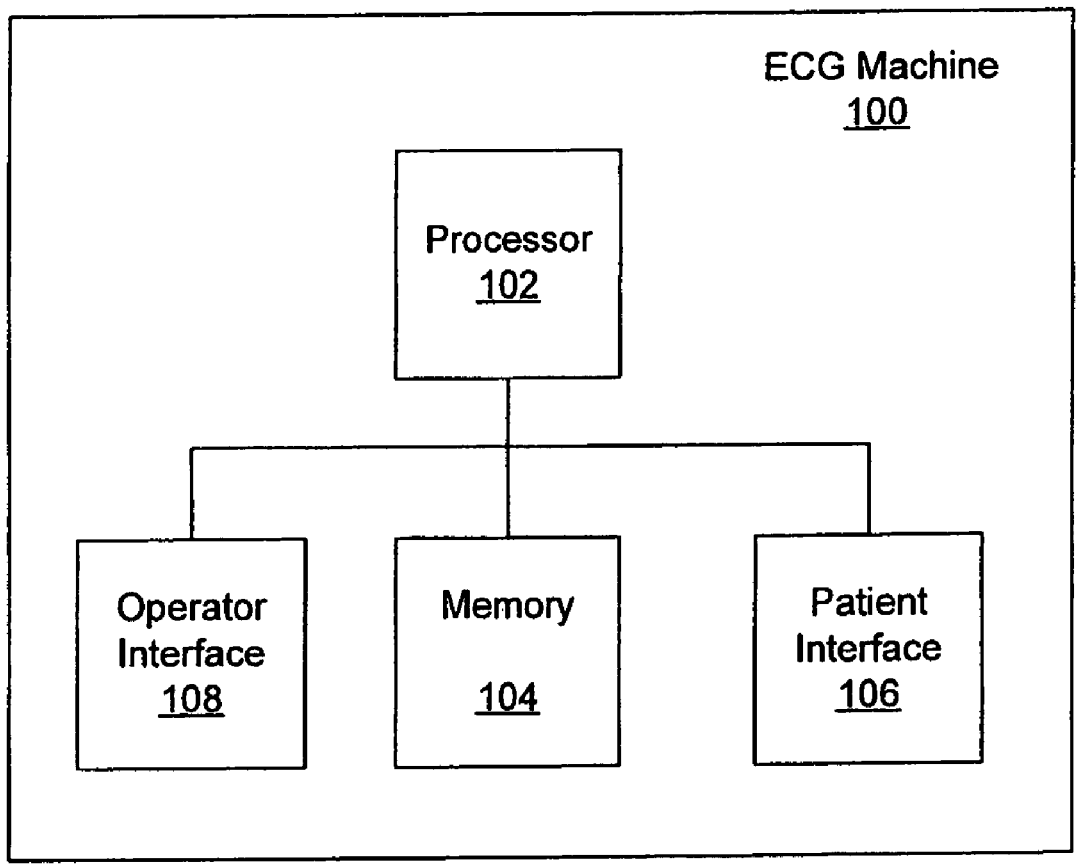
FIG. 1 is a representation of an implementation of an apparatus that comprises a processor, memory, patient interface, and operator interface.

Turning to FIG. 1, an implementation of an apparatus and/or ECG (electrocardiogram) machine 100 in an example comprises processor 102, memory 104, patient interface 106, and operator interface 108. The processor 102 comprises a filtering algorithm to extract the fetal ECG (fECG) from raw abdominal data. The memory 104 comprises a recordable data storage medium. The patient interface 106 comprises one or more pairs of electrodes to obtain measurements from a mother and fetus. For example, the patient interface 106 comprises surface electrodes placed on a pregnant woman's abdomen. The operator interface 108 comprises an operator console and a display to allow operation of the ECG machine 100 and output of data for review by a physician. The ECG machine 100 in an example comprises a digital ECG machine and/or an analog ECG machine. The processor 102 may incorporate an analog-to-digital converter (ADC) to convert analog abdominal input signals when the ECG machine 100 comprises an analog ECG machine, as will be appreciated by those skilled in the art.

The fECG is extracted from maternal ECG (mECG) early in the pregnancy, for example, week twenty to twenty of gestation and earlier. Extraction is based on a Blind-Adaptive-Filtering approach that overcomes the theoretical limitations in applying conventional Blind Signal Separation (BSS) methods based on ICA (independent component analysis) or AMUSE to this signal extraction problem and which greatly limited the extraction of fECG beyond the 30th gestation week (yielding very noisy separation even at these gestation weeks). Presented are separation results for actual maternal data down to 24th gestation week. The approach has no foreseeable limitation to be successful at earlier gestation weeks.

Presented is an algorithm that may be implemented in conventional (high resolution) ECG machines. The algorithm is noninvasive and conveniently accessible at a physician's clinic. Considered is the extraction of fECG from real patient data obtained with a high resolution and otherwise conventional ECG machine using 3 ECG surface electrode pairs placed on the skin of a pregnant woman.

The theoretical limitations on ICA or on AMUSE-based BSS, when the number of independent or uncorrelated source signals exceeds the number of electrode pairs, while the sources considered are not of negligible power, as is the case in raw abdominal ECG, led to a solution of the fECG extraction problem by employing a two-stage Blind Adaptive Filtering (BAF) approach, namely, to utilize the BAF's structure that allows estimation of certain parameters from the data, on the basis of a-priori or retrievable information on the nature of certain signals that are involved in a mixture, but which are NOT the signal while extraction is being sought. At least two BAF stages are employed in an exemplary implementation, as are at least two feature vectors, since a desired fECG signal is embedded in a raw signal that comprises two other classes of signal, each of very different features, one being mECG and the other being abdominal noise.

Figure 2:
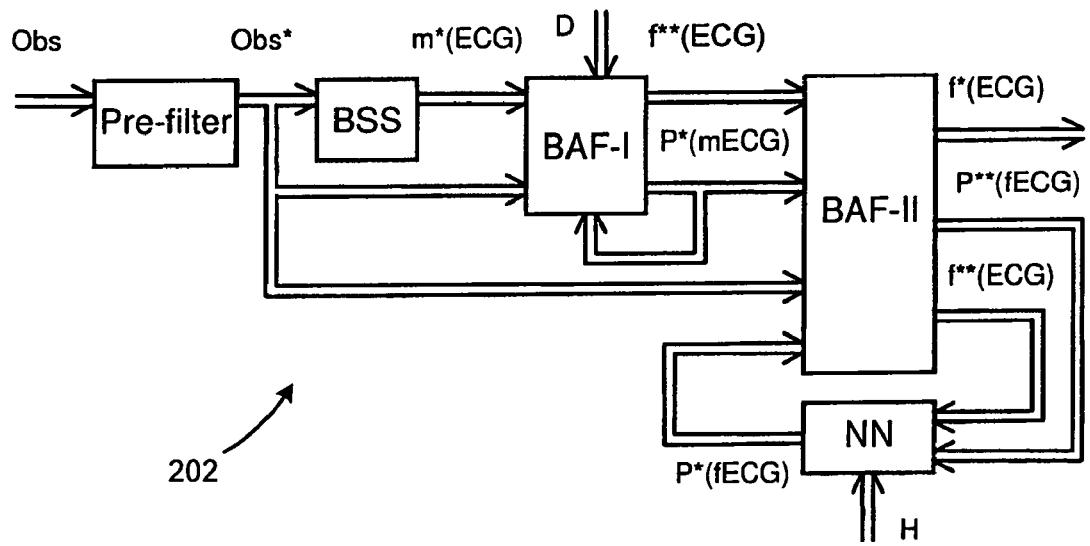
FIG. 2 is a representation of an implementation of exemplary logic executable by the processor of the apparatus of FIG. 1.

Turning to FIG. 2, the processor 102 in an example executes code in the memory 104 to provide exemplary logic 202. The logic 202 in an example is implemented in software and/or hardware of the ECG machine 100. The following exemplary Key 1 identifies exemplary representations employed in FIG. 2 for the logic 202.

Key 1:
  x**: initial estimate of . . .
  x*: final estimate of . . .
  P(.): parameters of (.)
  Obs: observations vector
  H: a-priori qualitative non-parametric features of ECG in general
  D: decision criterion on non-ECG noises (noting that fECG has negligible signal power compared with mECG or noise in the raw observations)
  NN: LAMSTAR Neural Network
  BSS: AMUSE-BASED BSS (not needed if maternal chest ECG channel is available) to be employed solely for mECG estimation The BAF extraction system of the ECG machine 100 employs these retrieved parameters in the logic 202 to filter and/or extract the desired signal.

The first BAF filter and/or stage (BAF-I) serves to estimate a set of candidate fECG signals from the observations. Noting that mECG dominates the observations, the first BAF stage receives mECG estimates from a pre-filtering stage that employs an AMUSE or an ICA-based BSS to extract a clean estimate of the mECG signal for the purpose of mECG parameter estimation by this first BAF stage. The first BAF stage also receives as input a non-parametric frequency-domain ECG feature vector (of frequency domain features common to any ECG signals). These, together with the mECG estimate above, yield at BAF-I output, a set of fECG candidate estimates, all of which satisfy the frequency domain features above while differing from the mECG. Subsequent to this estimation, the parameters of non ECG noise are estimated from the observations. The second BAF filter and/or stage (BAF-II) now receives the set (vector) of candidate fECG estimates and a vector of non-parametric time-domain features, also common to any ECG signal. The second BAF stage in an example incorporates a LAMSTAR Neural Network for selecting the fECG candidate estimates from the set of the candidate estimates which best fits the time-domain feature vector above while excluding the mECG estimate from that selection process. The BAF-II stage further employs a-priori frequency domain information to further reduce effects of non ECG (abdominal noise) noise in the selected fECG via employing a Wavelet Transform (WT) filter (Donohue filter) as part of BAF-II. The specificity of any harmonic filter considered in BAF-I already significantly reduces such noise. This two-stage BAF procedure thus avoids the earlier stated theoretical limitations of ICA or AMUSE-based BSS, which is employed here to get an improved estimate of the strongest raw source in the observations, namely, the mECG signal. It provides for the estimate to jointly satisfy both frequency and time domain features while excluding the mECG.

Figure 3:
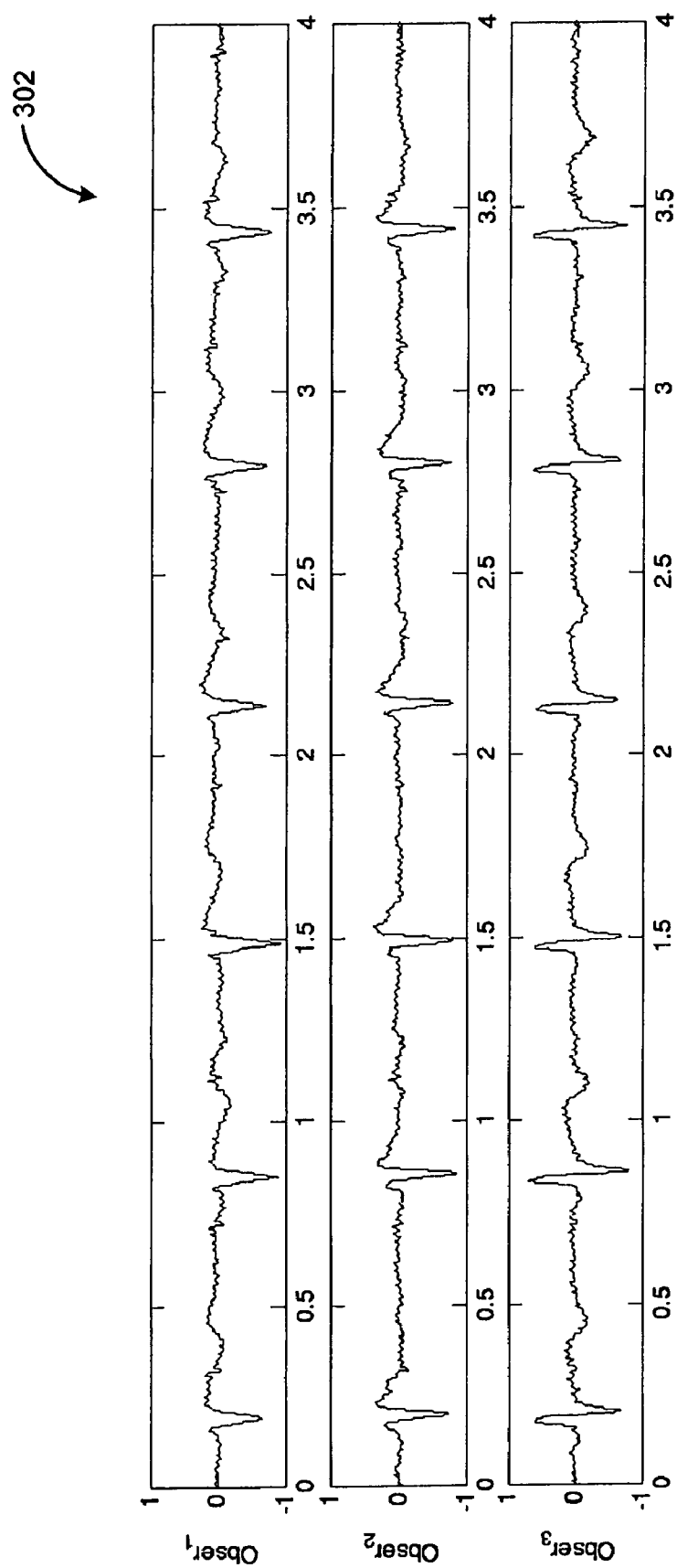
FIG. 3 represents a number of raw ECG signals that comprise raw ECG recordings from three conventional ECG electrode channels recorded on the abdomen of a pregnant mother at the 24th gestation week.
Figure 4:
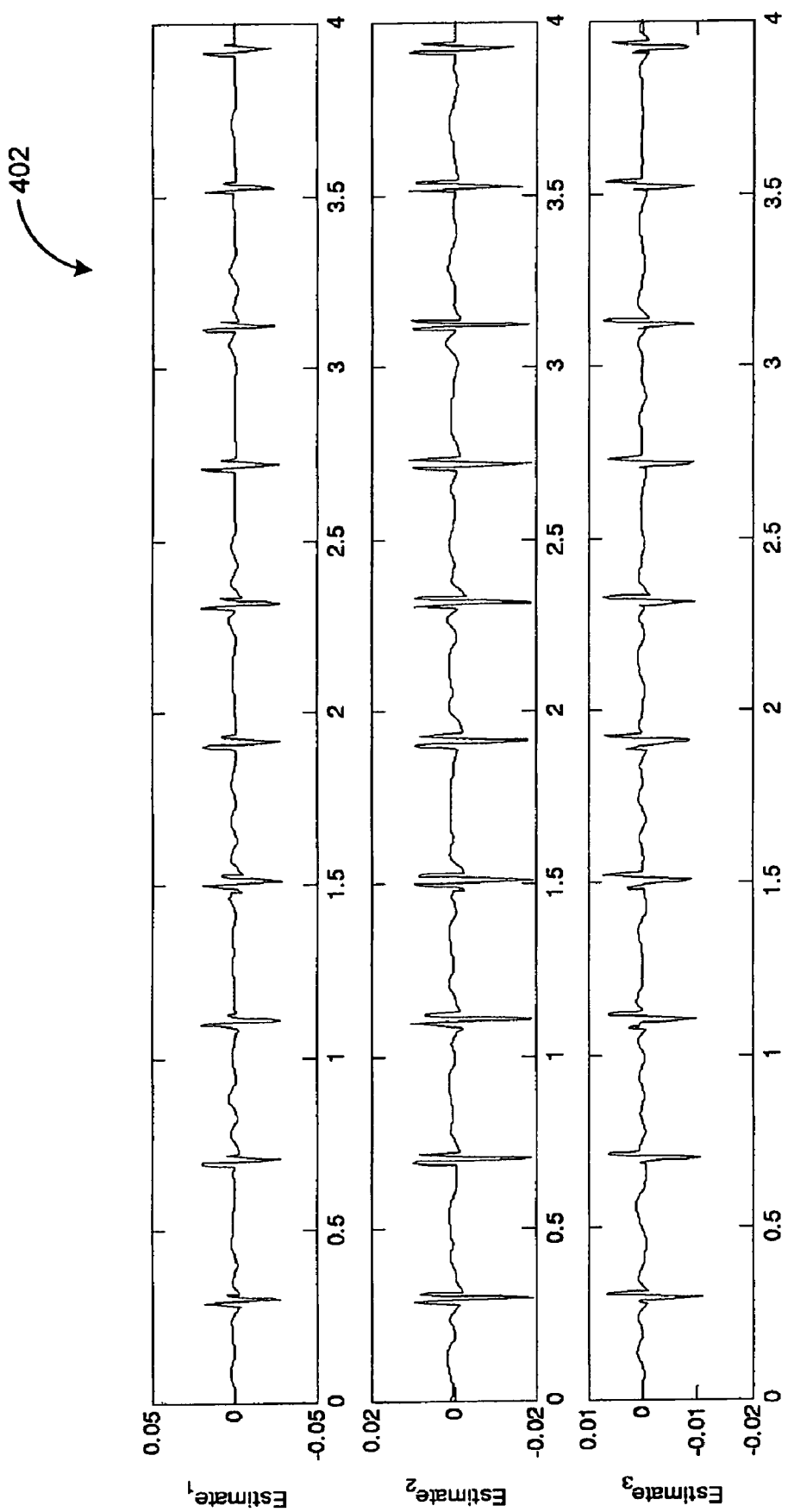
FIG. 4 is similar to FIG. 3 and represents a number of extracted fetal ECG (fECG) signals that correspond to the raw ECG signals of FIG. 3.

FIG. 3 represents a number of raw ECG signals 302. FIG. 4 represents a number of extracted fECG signals 402. The signal raw ECG signals 302 and/or the extracted fECG signals 402 in an example appear on the display of the operator interface 108. The raw ECG signals 302 in an example comprise raw ECG recordings from three conventional ECG electrode channels recorded on the abdomen of a pregnant mother at the 24th gestation week. The extracted fECG signals 402 in an example correspond to the raw ECG signals 302 and comprise the extracted fECG signals at the output of the second BAF stage (BAF-II) of the logic 202 of the ECG machine 100. The raw observations (recordings) are in terms of three channels. These were recorded on a high resolution ECG machine (resolution of 38 nanovolts per least significant bit; Sonicaid, a division of Huntleigh Healthcare Limited, 310-312 Dallow Road, Luton, Bedfordshire, United Kingdom, LU1 1TD, http://www.huntleigh-healthcare.com/, previously a subsidiary of Oxford Instruments plc, Old Station Way, Eynsham, Witney, Oxon OX29 4TL, http://www.oxinst.com/; e.g., as the ECG machine 100). Consistent with Doppler ultrasound, the extracted fECG of FIG. 4 shows an unambiguous fetal heart rate that is substantially higher than the (uncorrelated) maternal heart rate seen in FIG. 3.

The theoretical limitations on conventional (ICA or AMUSE) BSS-based fECG extraction, led to a design for the logic 202 of the ECG machine 100 to comprise a BAF (blind adaptive filtering) extraction system that employs a conventional BSS subsystem to improve the estimate of the mECG. The BSS subsystem in an example does not estimate the fECG. While the BAF system of the logic 202 in an example serves for blind separation, the BAF system in an exemplary implementation of the logic 202 comprises a blind filter serving for blind separation. This contrasts with ICA-based BSS systems or with AMUSE-based BSS systems. The logic 202 in an example incorporates an AMUSE algorithm (or alternatively, an ICA algorithm) in a supporting role to provide an estimate of the maternal signal to be subsequently used by the BAF system within, for example, the estimate is provided by a first stage BAF (BAF-I) of a two-stage BAF system that of the logic 202. This contrasts with a use of BSS for separation of the fECG signal.

The 2-stage BAF approach of the logic 202 is shown to retrieve fetal ECG (fECG) from actual patient's maternal ECG measurements at the 24th gestation week. On the basis of extrapolating the quality and clarity of the estimates from those obtained in two other sets of data, for the 20th gestation week and for the 21st week, and on the basis of experience gained from simulated data, it is believed that the BAF approach of the logic 202 should be able to extract fECG at earlier gestation weeks. For example, the BAF approach of the logic 202 should be able to extract fECG down to the 15th week. The results obtainable down to the 20th gestation week are superior to a previous report for real data.

A study proceeded without raw data from cases that involved fetal cardiac arrhythmia. It is expected that an exemplary application of the logic 202 can obtain good fECG extraction when requiring fECG parameter stationarity over at most two to three seconds. The discussion of the employment of the logic 202 in extraction of the fetal signal for ECG data applies analogously to employment of the logic 202 in extraction of the fetal signal for magnetocardiographic (MCG) data.

Figure 5:
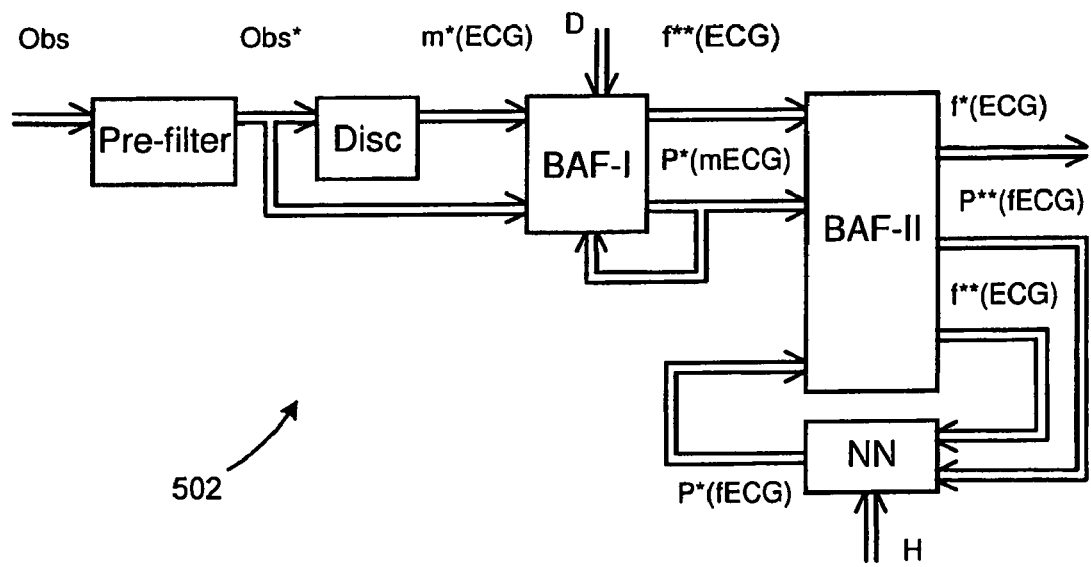
FIG. 5 is a representation of another implementation of exemplary logic executable by the processor of the apparatus of FIG. 1.

Turning to FIG. 5, the processor 102 in an example executes code in the memory 104 to provide exemplary logic 502. The logic 202 in an example is implemented in software and/or hardware of the ECG machine 100. The following exemplary Key 2 identifies exemplary representations employed in FIG. 5 for the logic 502.

Key 2:
  $x^{**}$: initial estimate of . . .
  $x^*$: final estimate of . . .
  P(.): parameters of (.)
  Obs: observations vector
  H: a-priori qualitative non-parametric features of ECG in general
  D: decision criterion on non-ECG noises (noting that fECG has negligible signal power compared with mECG or noise in the raw observations)
  NN: LAMSTAR Neural Network
  Disc: mECG discriminator
Referring to FIG. 5, in an example:
(1.) The Pre-Filter stage of the logic 502 comprises a cascade of:
  (1a.) A high-pass filter (HPF) to filter out DC in the raw observations obtained from the pregnant woman's abdomen, with a typical cutoff frequency at approximately 1 Hz.
  (1ai) A low pass filter to filter out high frequencies beyond the ECG spectrum.
  (1b.) A narrow Band-Pass Filter (BPF) array to filter out the power-line frequencies from the raw observations and which may comprise a sub harmonic band.
  (1c.) A Median Filter (MF) to reduce some of the noise and the mECG from the incoming raw observation, where this median filter may comprise two median sub-filters each being a MF of different parameters from the other and where the combined MF output is the difference between these two sub filters. The median filter may incorporate an averaged estimate of the R wave of the mECG, as derived from the raw ECG, for example, at the output of the narrow band-pass filter (BPF) array. Also, the median filter may be substituted by or combined with a wavelet-transform (WT) filter that removes the high-frequency components of the incoming signal that lie between the absolute-value peaks of the incoming signal and subtracting the WT filter's output from the input to that WT filter.
(2.) In the logic 502, the BSS element of the logic 202 is substituted by a discriminator element Disc. The discriminator element Disc comprises a simple absolute-value (time-domain) peak detector to retrieve the interval between the R-waves of the mECG, which correspond to the absolute-value peaks of the raw observations before the Pre-Filter stage. This interval value will further serve to discriminate between the fECG estimates and the mECG, noting that the fECG signal differs in its interval duration or rate from the mECG signal, as is an exemplary purpose of the BSS stage in the logic 202. The discrimination step (or discriminator stage) may also perform cepstral filtering of the output from the Pre-Filter stage of the logic 502, and then detect those peaks of the resulting cepstrum to retrieve a peak that does not lie near the origin but does not correspond to the rate of the mECG signal as detected earlier in the discriminator element Disc stage, but which is not close to zero quefrency. Note: "quefrency" is the term used in Cepstral Analysis to denote the cepstral "frequency". This cepstral information may be subsequently used to improve the efficiency of the following BAF-I stage and the BAF-II stage, including the post filtering element sub-stage of the BAF-II stage, for example, by providing an initial estimate of the base-frequency used in the BAF-I stage.
(3.) The BAF-I stage of the logic 202 and/or the logic 502 receives frequency domain feature-input information (denoted as "D" in the logic 202 and the logic 502) which is the average spectral feature of any ECG signal for any base ECG repetition frequency (rate), such that the first BAF (blind adaptive filtering stage denoted "BAF-I" in the logic 202 and the logic 502) is a set (for example, a multitude, an array) of harmonic BPF filter bands (HFBs) jointly denoted as a harmonic filter array (HFA), and whose input is the output from the Pre-Filter stage of the logic 202 and/or the logic 502 stage, while the output of the discriminator element Disc stage serves to avoid the base repetition frequency of the mECG signal as determined in the discriminator element Disc stage. The base-frequencies of the individual HFB's of the harmonic filter array (HFA) differ by a small frequency incremental value and the multitude of HFBs serves to cover a sufficiently large range of base frequencies. This difference in the base frequency value determines the resolution of the whole extraction system, since the fECG duration (and hence, its repetition frequency) is a-priori unknown. Therefore, by employing many harmonic BPF filter bands, each differing slightly in its base-frequency, one can (reliably) ensure that at least one of the HFBs in the array (multitude) employs a base-frequency that is very close to that of the (yet undetected) fECG signal and hence, a reliable estimate of the fetal signal that is imbedded in the raw observations. To allow the following of fast changes in interval between fECG R-waves (denoted as the duration of an fECG cycle,) as used in the case of arrhythmias, the harmonic filters receive approximately a four second string of data per each run and then reset themselves. Also, several such data strings are run simultaneously, each being delayed from the other by, for example, one second, to allow following of arrhythmias that change from one second to the next.

(4.) Stage BAF-II of the logic 202 and/or the logic 502 receives at its input a vector of time-domain frequency features and the outputs of each of the multitude of harmonic filter bands (HFBs) related to a multitude of base frequencies of candidate fECG signals. If data is from gestation week twenty-two or earlier, the harmonic filters outputs, denoted as f**(ECG) may first be raised by a power n, where n is an odd integer, for example, three or five. The BAF-II stage selects a particular output signal from the array (multitude) of output signals of BAF-I, as determined by a Neural Network (NN) component of BAF-II of the logic 202 and/or the logic 502, to best fit a time domain feature-input (H in the logic 202 and/or the logic 502) received by the BAF-II stage. The NN serves as a decision element for BAF-II, to determine which of the harmonic arrays of the BAF-I stage is that which most closely satisfies the time-domain feature-input H. Feature H is formulated as the time-domain feature of any ECG signal in terms of high absolute amplitude of the narrow time interval around the R wave and the much lower absolute value amplitudes of the much wider time interval over the T, U, P parts of the ECG signal. Additional exemplary details in this regard are presented in connection with TABLE 1 herein.

In an example, the NN employed in the logic 202 and/or the logic 502 may be the LAMSTAR NN network. The NN determines that particular harmonic filter band of the BAF-I stage, whose output minimizes the distance of a distance function formulated in the main body of the BAF-II component, between H and any of the outputs of the various HFBs of the harmonic filter array of the BAF-I stage. The NN's decision is sent to BAF-II which then outputs the particular harmonic BPF band selected by the NN to the post filtering element sub-stage of the BAF-II stage.

In another example, the NN is substituted with a modified (compressed) correlation function $C(k,t')$ which correlates each of the outputs f(ECG) of the harmonic filter arrays (or these outputs f(ECG) when raised by a power n) and the output of the narrow Band-Pass Filter (BPF) array of the Pre-Filter stage of the logic 502 when compressed by a factor m (after being raised by power n, whenever the outputs f** (ECG) are raised by that power), the factor m being the ratio of the base frequency of a given harmonic filter array and the inverse of the duration of the raw input as determined in the BAF-I stage.

(5.) In the logic 202 and/or the logic 502, a post filtering element (sub-stage) is imbedded in the BAF-II, which serves to remove non-ECG noises from the BAF's output. This filter is based on the a-priori assumption that the P, T, U components of any ECG signal (namely the ECG section between two successive QRS components) are of low frequency (LF) only. It receives at its input the first estimate of the fECG signal and generates the final estimate of the fECG signal.

The post filtering sub-stage of BAF-II is a Wavelet Transform (WT) filter that exploits the time-frequency nature of WT by removing high frequency (HF) only between the absolute-value peaks of the input to the WT filter (as appear in the output of the BAF-I stage. This implies WT-ing the post-filter's input, setting to zero for frequencies above some reasonable threshold frequency (for example, 20 or 30 Hz), and inverse WT-ing the outcome. The WT filter thus further removes non-ECG noises (mainly abdominal myoelectric activity) not yet filtered in the NN-selected HFB. If the BAF-II stage has involved raising the input to the BAF-II stage by power n, then the input to the WT-filtering above is first raised by raising the output of the WT.

Alternatively, the post filter element (sub-stage) of the BAF-II stage can be considered as a separate filtering stage to follow the second blind adaptive filter stage of the BAF-II stage, producing, at its output, the final estimate of the fECG signal.

(6.) In another exemplary logic locatable in the memory 104 and executable by the processor 102, the BAF I is employed first to produce a filtered estimate of the MECG that is subsequently employed to substantially reduce the effect of the mECG in the input to the BAF-I and BAF-II stages of the logic 502.

(7.) PR and QT duration determination from the extracted fECG above are obtained by averaging of several (e.g., ten) adjacent extracted fECG waves and/or by curve fitting on fECG waves.

In an implementation, a signal that comprises maternal electrocardiogram (mECG) information, fetal electrocardiogram (fECG) information, and non-electrocardiogram noise is input into a first blind adaptive filter (BAF) stage. Frequency domain feature information is employed at the first blind adaptive filter stage to tune an array of harmonic filter bands. In an example, each of the harmonic filter bands in the array has a different base frequency, but each has the same basic spectral feature structure that is common to all electrocardiogram signals. The first blind adaptive filter stage generates a maternal electrocardiogram parameter estimate, a non-electrocardiogram noise parameter estimate, and a set of outputs of the array of harmonic filter bands. The outputs of the first blind adaptive filter stage are input into a second blind adaptive filter stage. The second blind adaptive filter stage serves to determine which of the various outputs of the array of harmonic filter bands of the first blind adaptive filter stage is an estimate of the fetal electrocardiogram. This determination is made at the second blind adaptive filter stage by employing a time domain feature vector of the basic time domain features of any electrocardiogram signal and by using the base frequency of the maternal electrocardiogram as also estimated in the first blind adaptive filter stage. A correct base frequency of a harmonic filter band yields an electrocardiogram signal that is embedded in the input to the first blind adaptive filter stage, while the wrong harmonic filter band yields a nonsense signal. By excluding the maternal electrocardiogram base frequency, then only the fetal electrocardiogram will satisfy the time domain features, to yield an initial estimate of the fetal electrocardiogram signal at the second blind adaptive filter stage.

Subsequently, one or more sets of selected time samples between the time domain peaks of the initial estimate of the fetal electrocardiogram signal are filtered in BAF-II to remove noise from the initial estimate of the fetal electrocardiogram signal. This noise is in frequency ranges well outside those of any electrocardiogram signal component that lies between the time domain peaks, thus yielding the final fetal electrocardiogram estimate of the second stage of blind adaptive filtering. In an example, this step, the filtering of noise is achieved by incorporating a Wavelet Transform filter (WTF) element as a final element of the second blind adaptive filter stage. The Wavelet transform filter thus serves to remove undesired frequencies at automatically-selected particular time intervals.

In an example, a signal that comprises maternal electrocardiogram information, fetal electrocardiogram information, and non-electrocardiogram noise is input into a first blind adaptive filter stage. A feature vector of basic frequency domain features that are common to electrocardiogram signals is employed at the first blind adaptive filter stage to generate a maternal electrocardiogram parameter estimate and a set of candidate fetal electrocardiogram estimates that satisfy the feature vector of basic frequency domain features. The maternal electrocardiogram parameter estimate satisfies the feature vector of basic frequency domain features. The set of candidate fetal electrocardiogram estimates satisfies the feature vector of basic frequency domain features. The maternal electrocardiogram parameter estimate and the set of candidate fetal electrocardiogram estimates are then input into a second blind adaptive filter stage. A feature vector of basic time domain features that are common to electrocardiogram signals is employed at the second blind adaptive filter stage to extract an initial estimate of the fetal electrocardiogram signal that satisfies the feature vector of basic time domain features. One or more sets of selected time samples of the fetal electrocardiogram signal estimate are then filtered to remove noise from the initial estimate of the fetal electrocardiogram signal to produce the final estimate of the fetal electrocardiogram signal.

In an exemplary study of fECG extraction an exemplary objective was to extract fECG from mECG obtained using surface electrodes placed on a pregnant woman's abdomen. In an exemplary study design, both mECG and abdominal noise can be orders of magnitude stronger than fECG signal. Abdominal surface electrodes were used to obtain a three channel ECG with a high resolution ECG machine (Oxford Instruments plc, Old Station Way, Eynsham, Witney, Oxon OX29 4TL, http://www.oxinst.com/; e.g., as the ECG machine 100). Using electronic recordings of data obtained between gestational age of twenty weeks and term, a filtering and extraction algorithm was used to obtain the fECG. Pre-filtering was initially performed with a high pass filter, followed by a two-stage Blind Adaptive Filter (BAF). The first stage BAF was used to reduce effects of abdominal noise from the fECG embedded in the mECG. The second BAF stage then extracted the fECG by further removing mECG and abdominal noise. No a-priori fECG timing or rate information is assumed during the filtering process.

Ten ECG tracings were obtained at gestational ages from twenty to thirty-eight weeks. In each case fECG was isolated. The extracted signals demonstrate an uncorrelated, unambiguous cardiac rate significantly faster than the maternal rate. The combined filter allowed identification of the QRS complex and the P and T waves.

Figure 6:
FIG. 6 represents a raw ECG signal for the 21st week of gestation at the time of 0 to 2 seconds.
Figure 7:
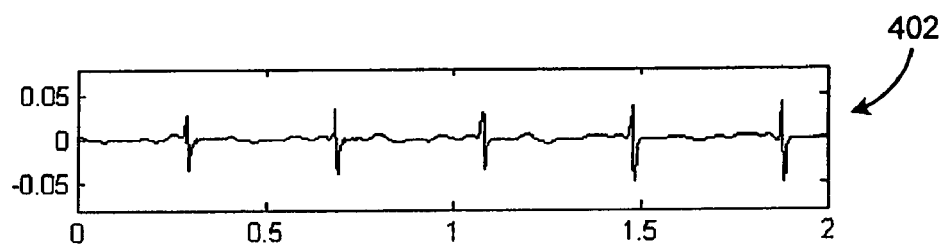
FIG. 7 represents an extracted fECG signal for the 21st week of gestation at the time of 0 to 2 seconds, where the extracted fECG signal corresponds to the raw ECG signal of FIG. 6.

FIGS. 6 and 7 show unprocessed mECG and extracted fECG, respectively. The raw ECG signal 302 in an example comprises unprocessed MECG for the 21st week of gestation at the time of 0 to 2 seconds. The extracted fECG signal 402 in an example corresponds to the raw ECG signal 302 and comprises the extracted fECG for the 21st week of gestation at the time of 0 to 2 seconds. Evaluation of fECG is expected to have importance in diagnosing, and monitoring treatment of fetal arrhythmias. As described herein, fECG can be acquired from surface maternal electrodes as early as twenty weeks gestational age.

Whereas Doppler ultrasound devices provide adequate fetal heart rate, namely, the RR interval information, it is recognized that easy access to fECG is much desired, due to the diagnostic importance of the whole PQRST complex, and especially PR and QT durations. PR durations play a major role in diagnosing cardiac arrhythmias due to pre-excitation, such as the Wolff Parkinson-White (WPW) Syndrome whose prevalence is estimated at 0.15-0.3% of the pediatric population. Sudden death in pre-excitation syndrome in childhood may reach 0.5%. The QT durations are significant in diagnosing the Long QT Syndrome (LQTS). LQTS has also been shown to be one of the etiologies of Sudden Infant Death Syndrome (SIDS).

Hence, diagnosis via mECG exams of expectant mothers during an office visit is desirable, noting the convenience and speed of ECG tests. Early detection (weeks twenty to twenty-five of gestation) with correct diagnosis will also aid in drug selection and continued monitoring.

Figure 8:
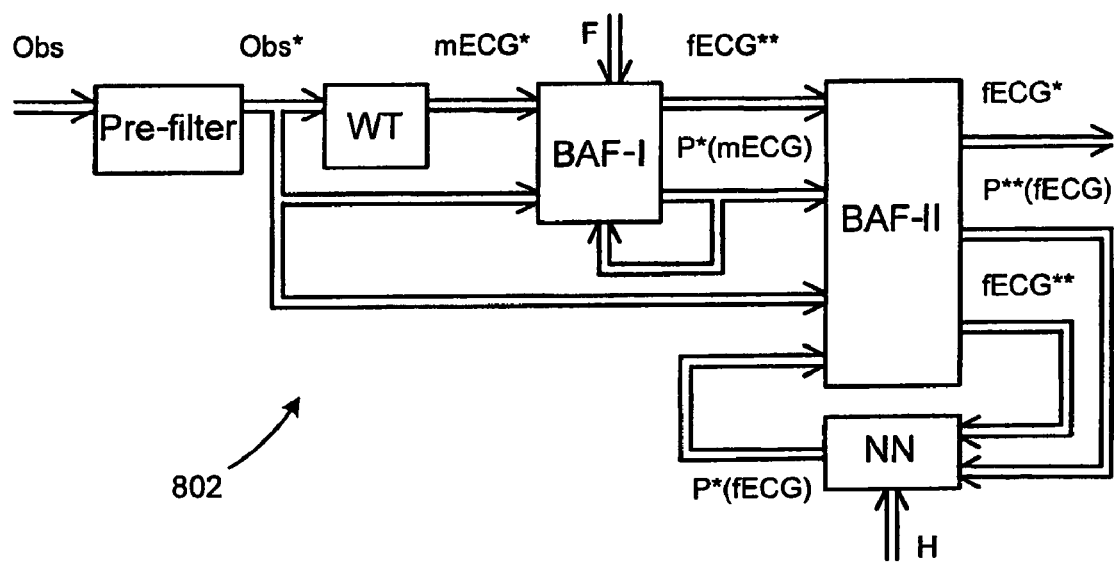
FIG. 8 is a representation of a further implementation of exemplary logic executable by the processor of the apparatus of FIG. 1.

Turning to FIG. 8, the processor 102 in an example executes code in the memory 104 to provide exemplary logic 802. The logic 802 in an example is implemented in software and/or hardware of the ECG machine 100. Referring to FIGS. 1 and 8, both mECG and abdominal (mainly electromyogram, EMG) noise can be orders of magnitude stronger than fECG signal. Abdominal surface electrodes (e.g., as the patient interface 106) were used to obtain a three channel ECG with a high resolution ECG machine (Sonicaid, a division of Huntleigh Healthcare Limited, 310-312 Dallow Road, Luton, Bedfordshire, United Kingdom, LU1 1TD, http://www.huntleigh-healthcare.com/, previously a subsidiary of Oxford Instruments plc, Old Station Way, Eynsham, Witney, Oxon OX29 4TL, http://www.oxinst.com/; e.g., as the ECG machine 100). Using electronic recordings of data obtained between gestational age of twenty weeks and term, a filtering and extraction algorithm (e.g., in the memory 104) was used (e.g., by the processor 102 and the operator interface 108) to obtain the fECG in an automated manner. The raw data was obtained at 16 bits per sample, 3000 samples/sec. at a resolution of 38 nanovolts/least-significant-bit. Pre-filtering was initially performed with a low pass filter (cutoff at 150 Hz). Subsequently, a two-stage Blind Adaptive Filter (BAF) was employed. The first stage BAF was used to reduce effects of abdominal noise from the fECG embedded in the (abdominal) mECG. The second BAF stage, incorporated a LAM-STAR (large scale memory storage and retrieval) neural network, then extracted the fECG by further removing mECG and abdominal noise.

The following exemplary Key 3 identifies exemplary representations employed in FIG. 8 for the logic 802.

Key 3:
(.)**: initial estimate of (.)
(.)*: final estimate of (.)
P(.): parameters of (.)
Obs: observations vector
H: a-priori time domain feature vector
F: a-priori frequency domain feature vector
NN: LAMSTAR Neural Network
WT: wavelet-based filter (including median filtering)

Ten raw abdominal ECG records were obtained at gestational ages from twenty to thirty eight weeks. In each case fECG was isolated. Of these, five abdominal ECG records, relating to gestation weeks twenty to twenty-four are discussed in detail herein, for illustrative purposes. The extracted signals demonstrate an uncorrelated, unambiguous cardiac rate significantly faster than the maternal rate. The combined filter allows identification of the QRS complex and the P and T waves.

Figure 17:
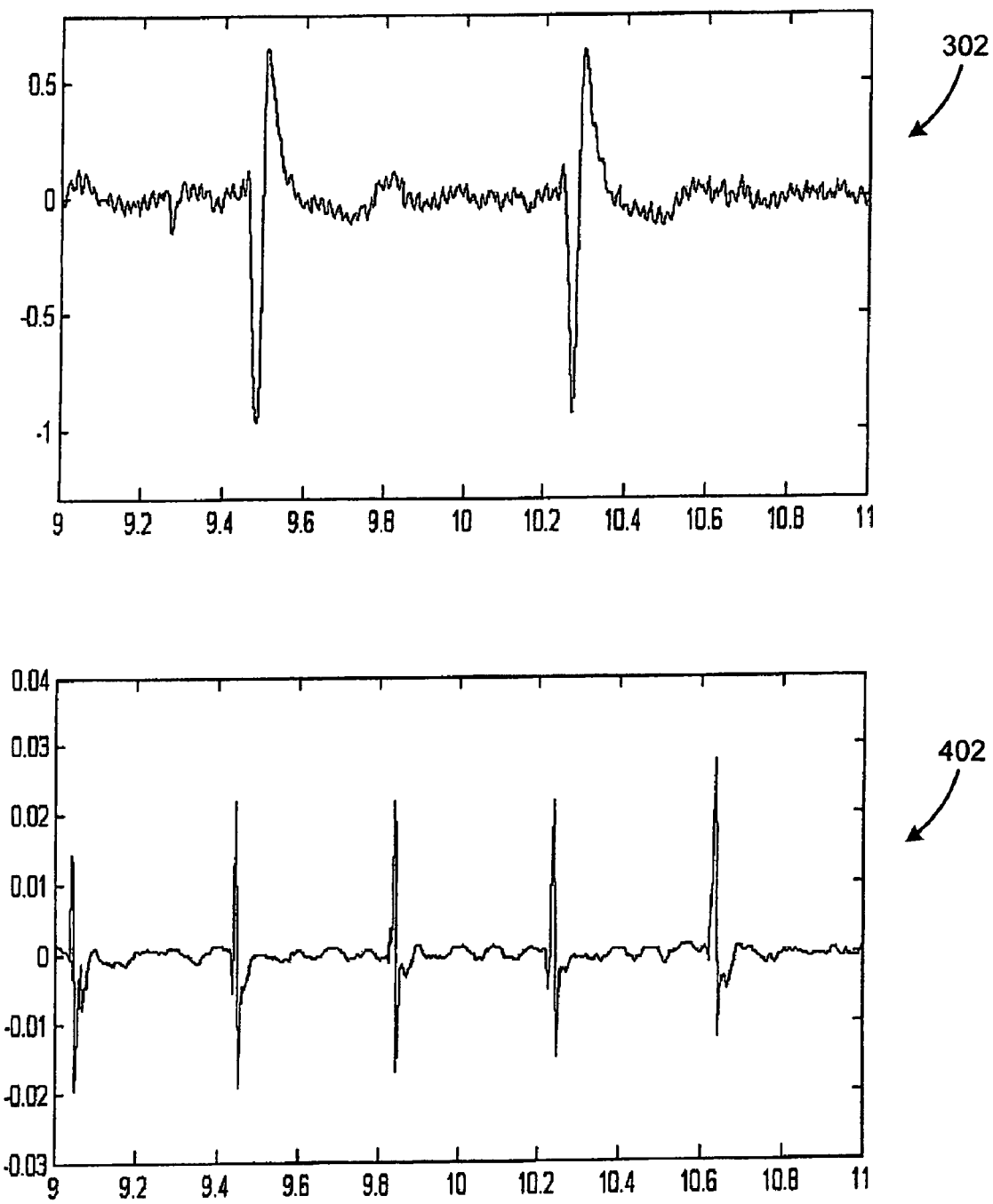
FIG. 17 is similar to FIG. 13 and shows the time of 9 to 11 seconds, for patient C.
Figure 18:
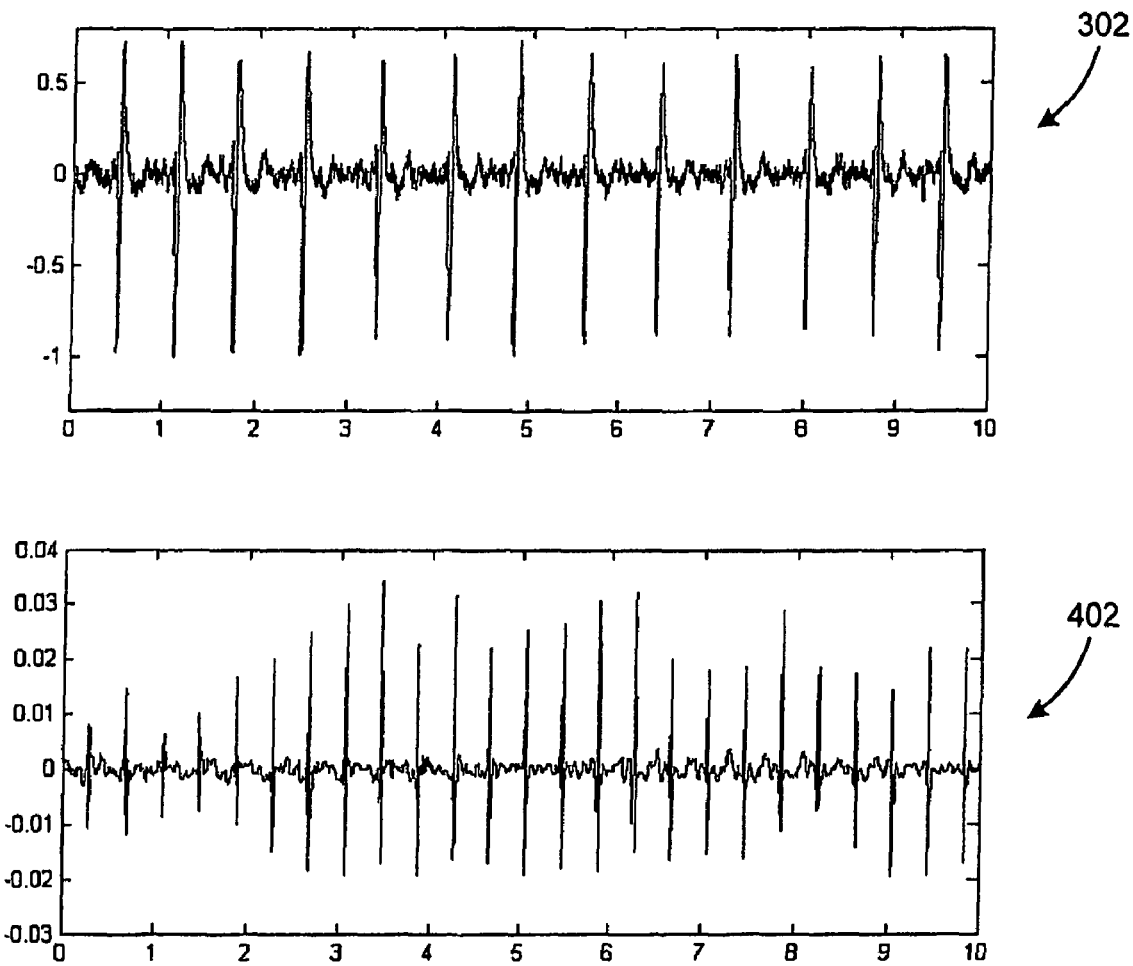
FIG. 18 is similar to FIG. 13 and shows the time of 0 to 10 seconds, for patient C.
Figure 19:
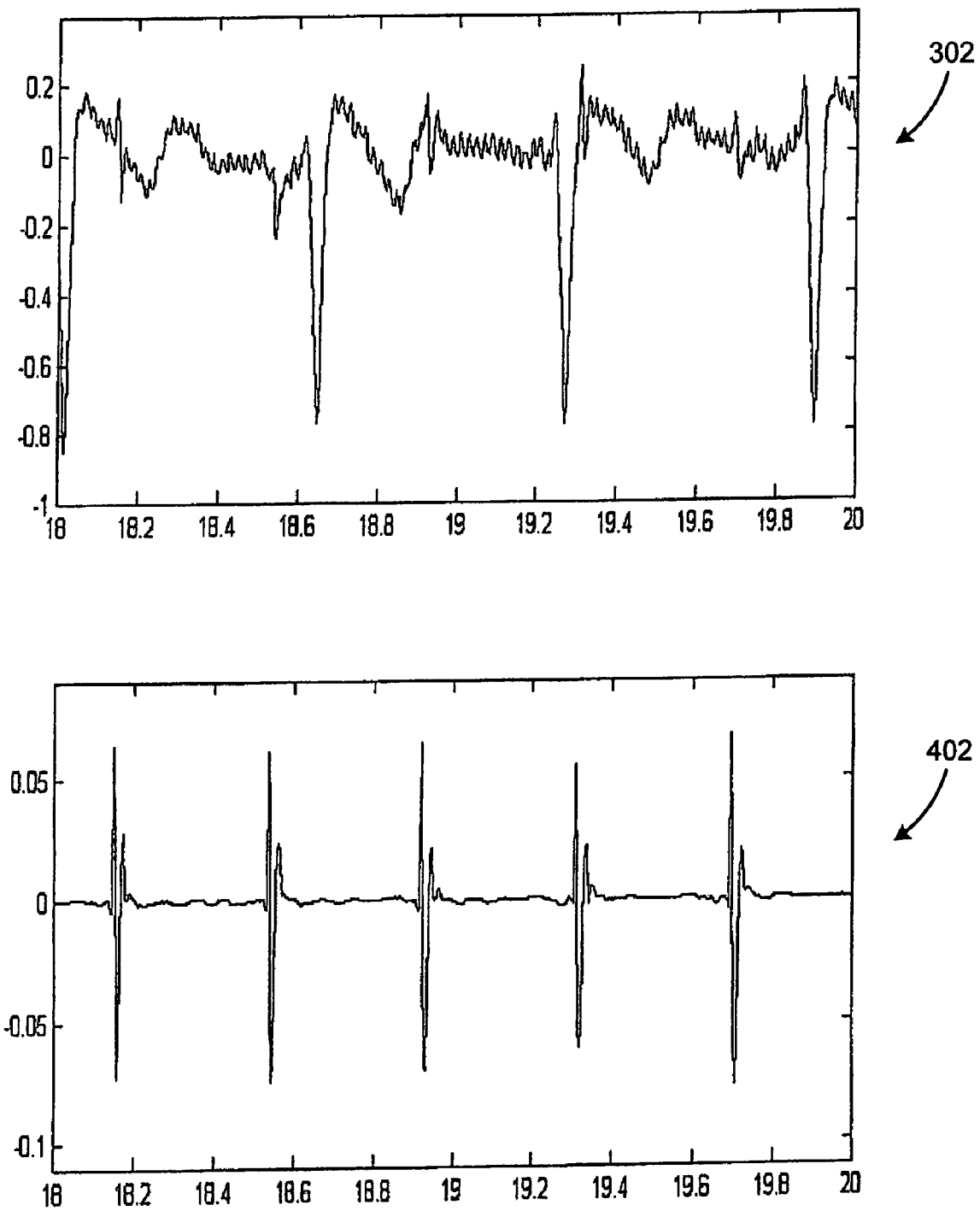
FIG. 19 shows the raw abdominal ECG and corresponding extracted fECG for the 24th week of gestation at the time of 18 to 20 seconds.
Figure 20:
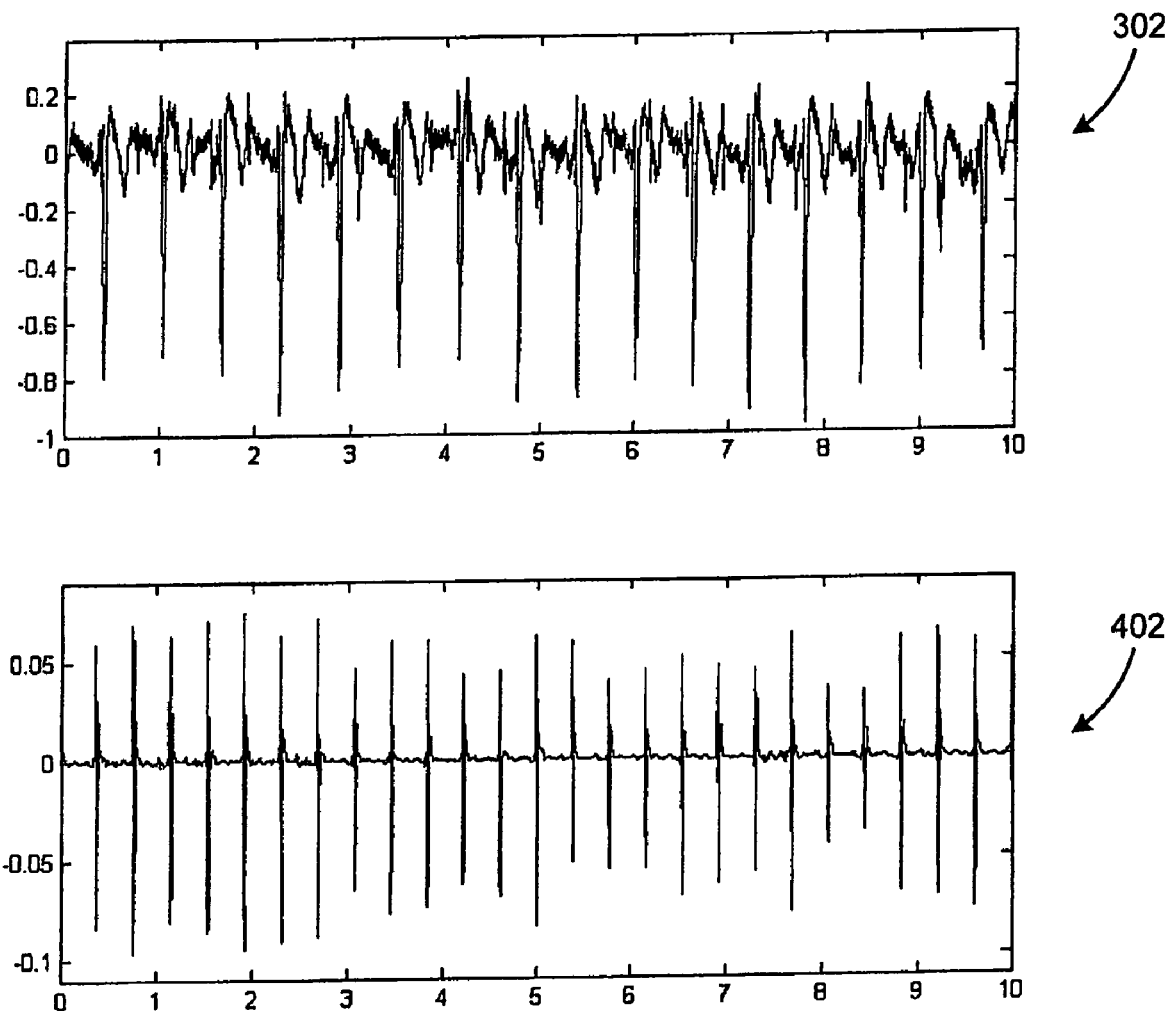
FIG. 20 is similar to FIG. 19 and shows the time of 0 to 10 seconds.

FIGS. 9 to 20 show unprocessed abdominal mECG from women at twenty to twenty four weeks of gestation with the corresponding extracted fECG signal. FIGS. 9 to 12 show the 20th week of gestation, FIGS. 13 to 18 show the 21st week of gestation for three patients (A, B, and C), and FIGS. 19 to 20 show the 24th week of gestation.

Figure 9:
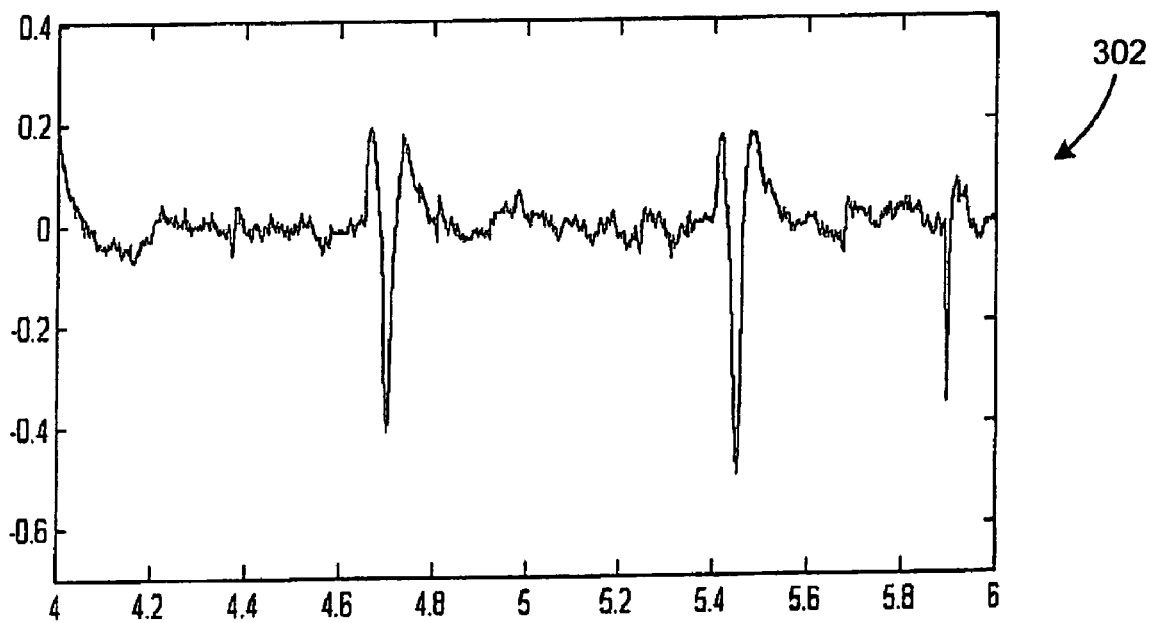
FIG. 9 shows the raw abdominal ECG and corresponding extracted fECG for the 20th week of gestation at the time of 4 to 6 seconds.
Figure 9:
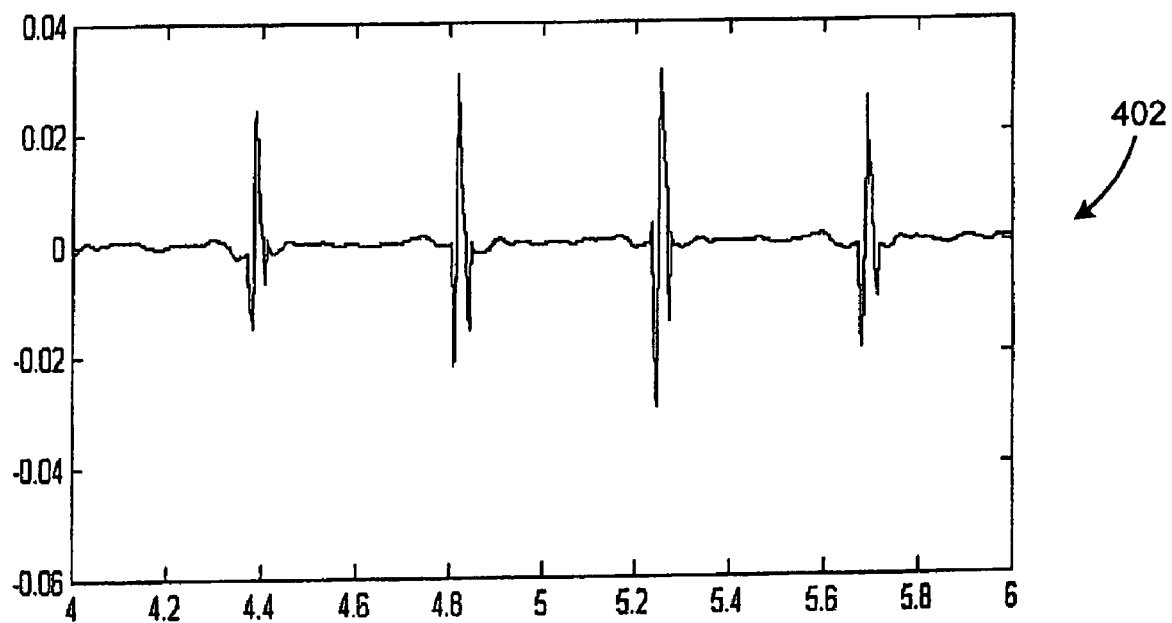
Figure 10:
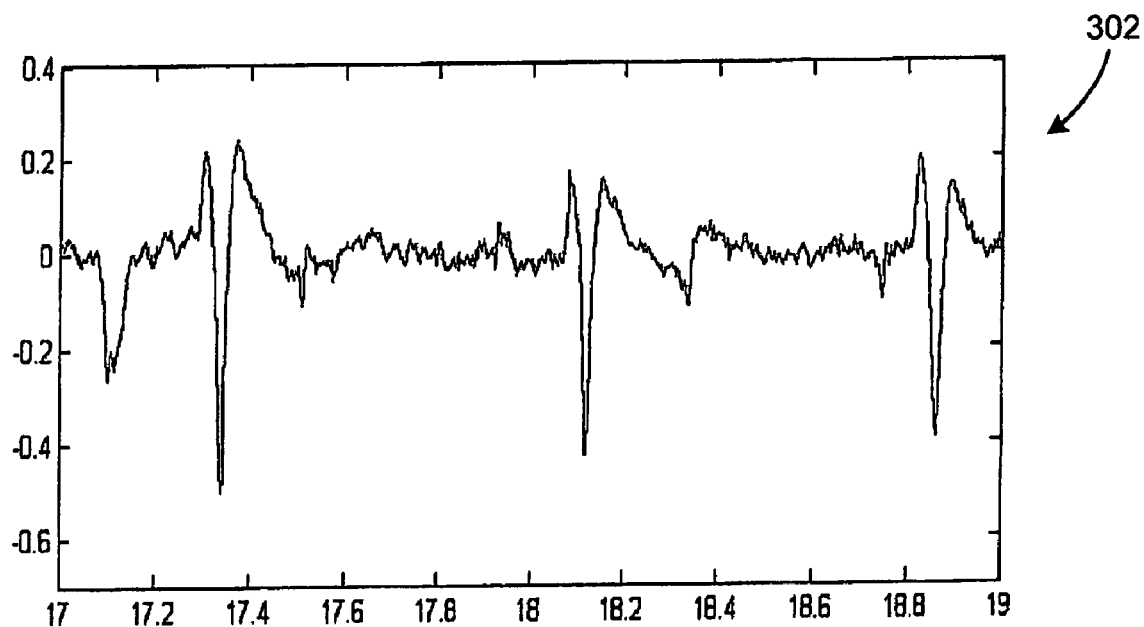
FIG. 10 is similar to FIG. 9 and shows the time of 17 to 19 seconds.
Figure 10:
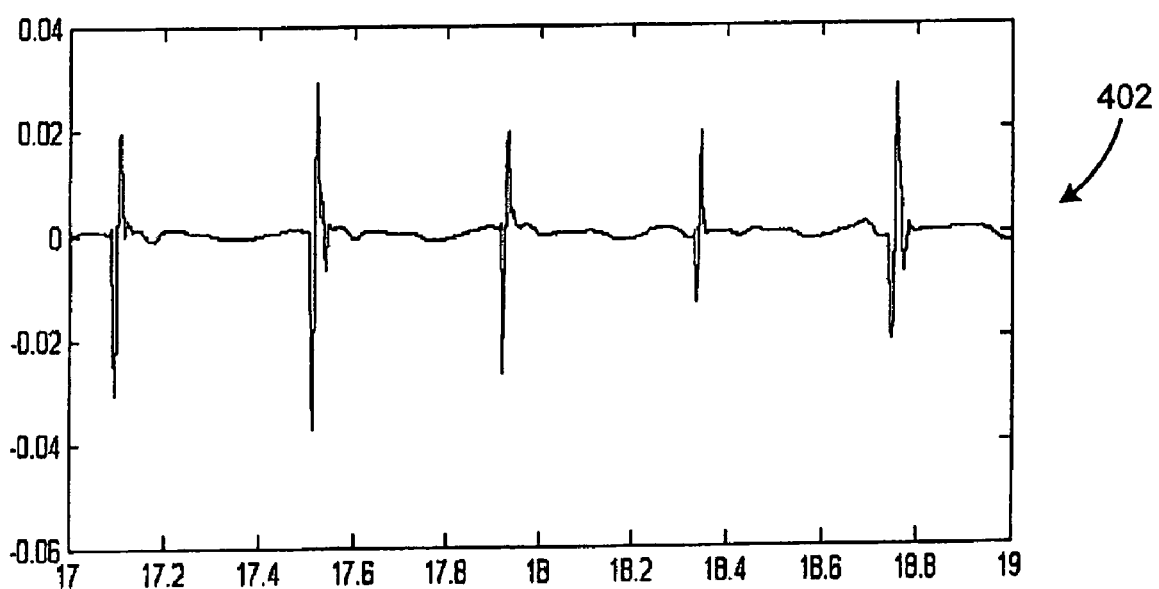
Figure 11:
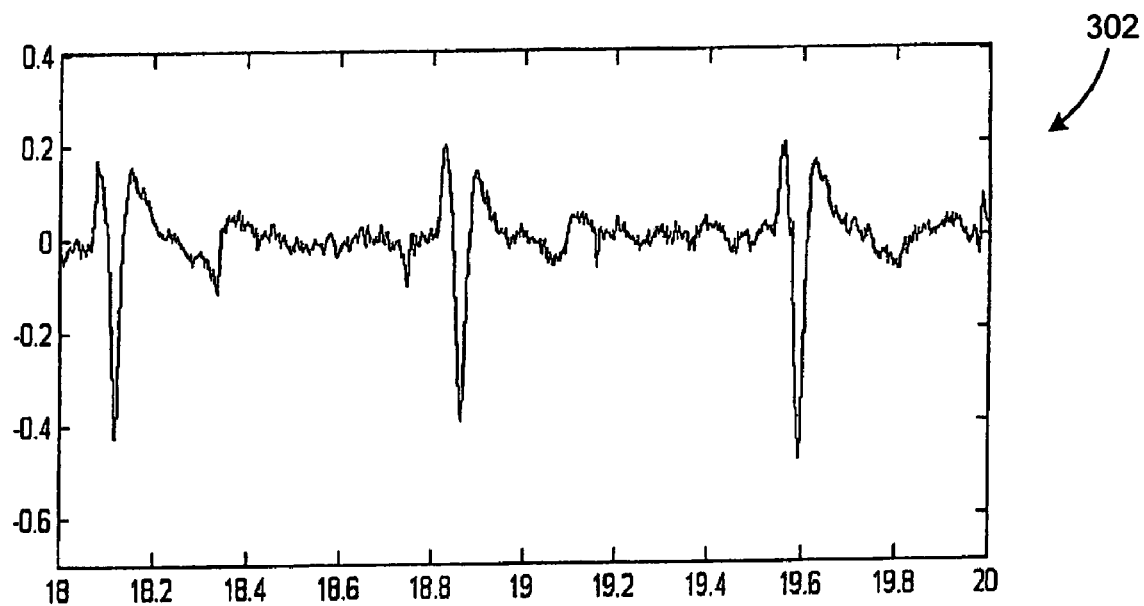
FIG. 11 is similar to FIG. 9 and shows the time of 18 to 20 seconds.
Figure 11:
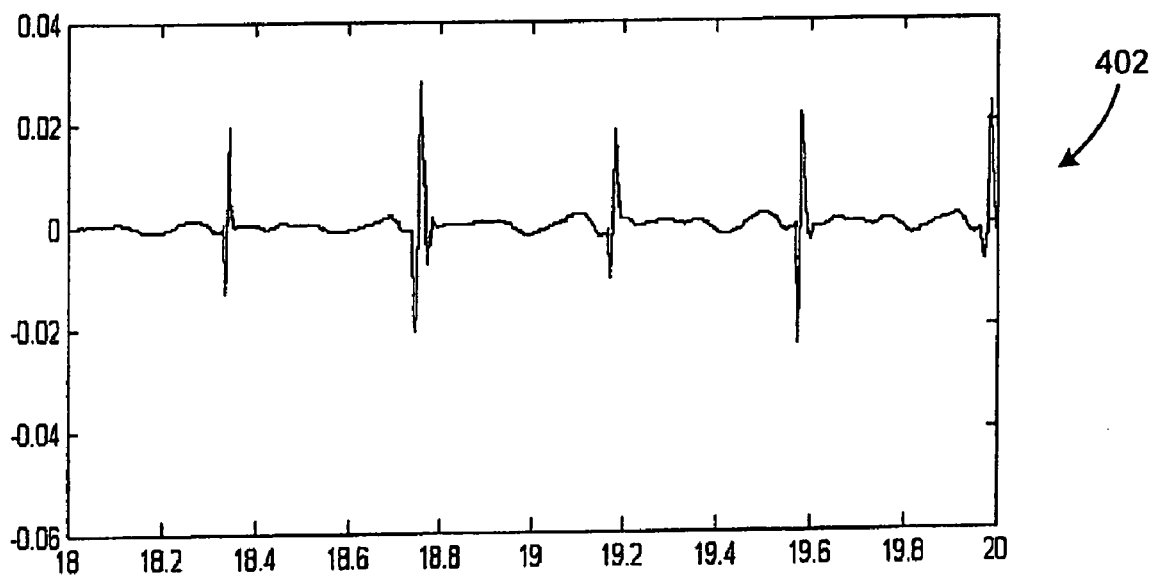
Figure 12:
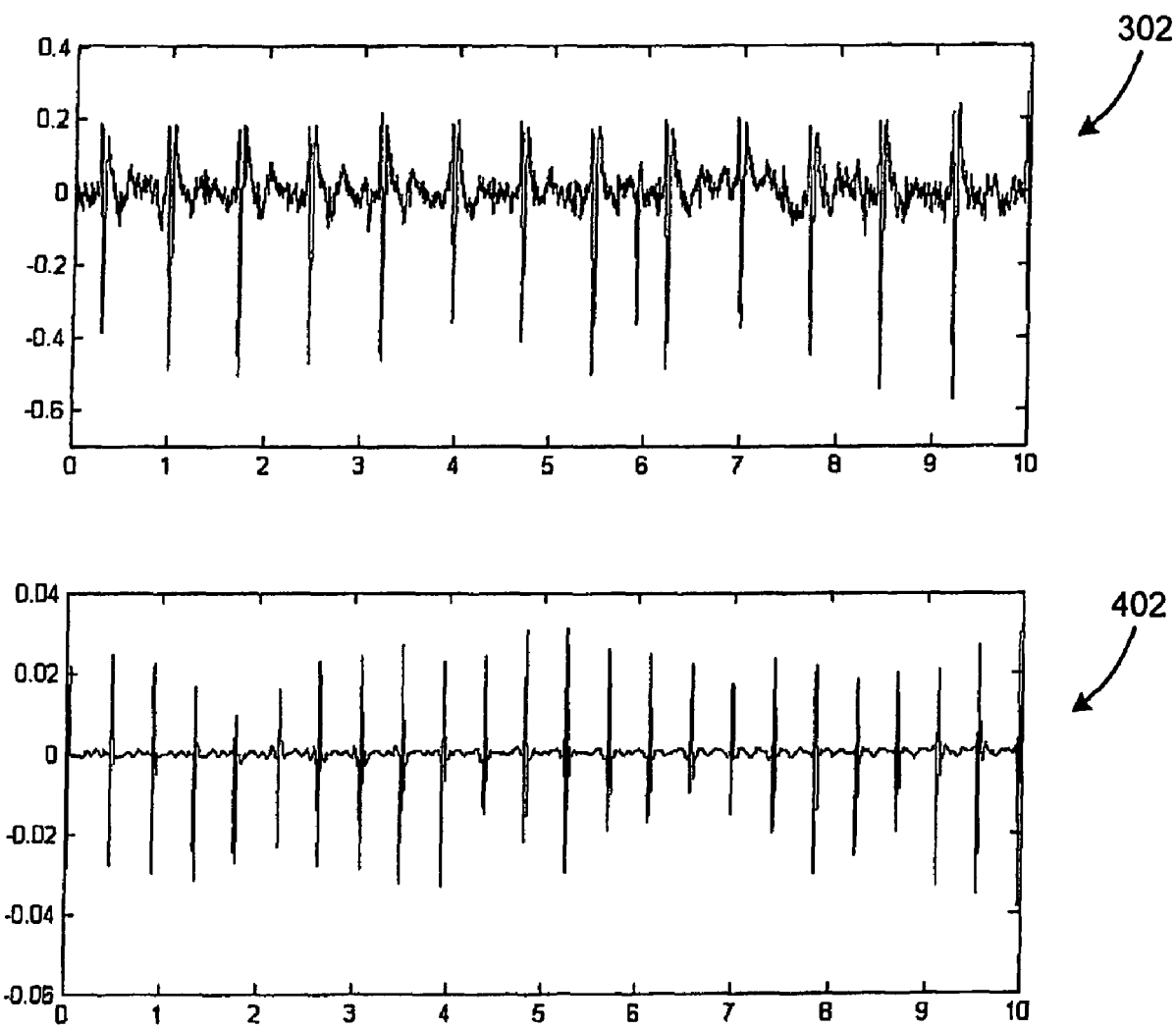
FIG. 12 is similar to FIG. 9 and shows the time of 0 to 10 seconds.

In particular, FIG. 9 shows the raw abdominal ECG and corresponding extracted fECG for the 20th week of gestation at the time of 4 to 6 seconds. FIG. 10 shows the time of 17 to 19 seconds. FIG. 11 shows the time of 18 to 20 seconds. FIG. 12 shows the time of 0 to 10 seconds.

Figure 13:
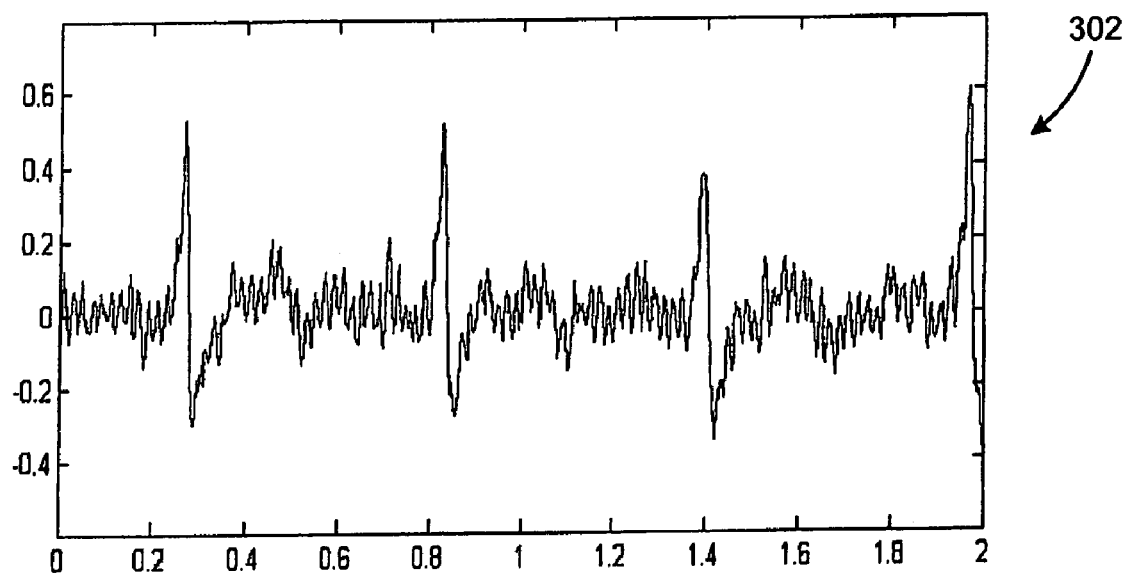
FIG. 13 shows the raw abdominal ECG and corresponding extracted fECG for the 21st week of gestation at the time of 0 to 2 seconds, for patient A.
Figure 13:
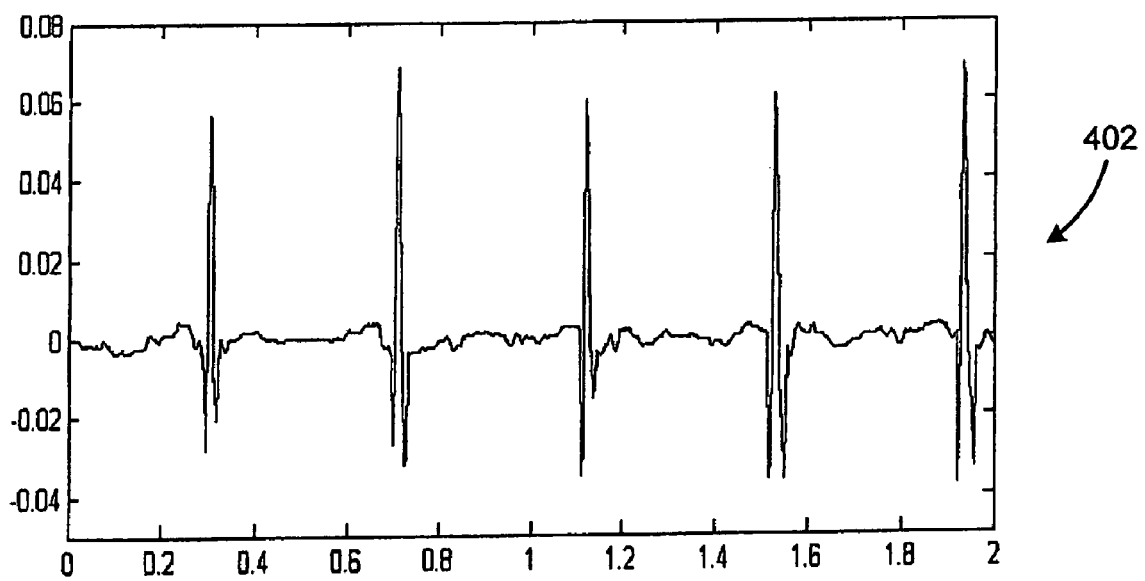
Figure 14:
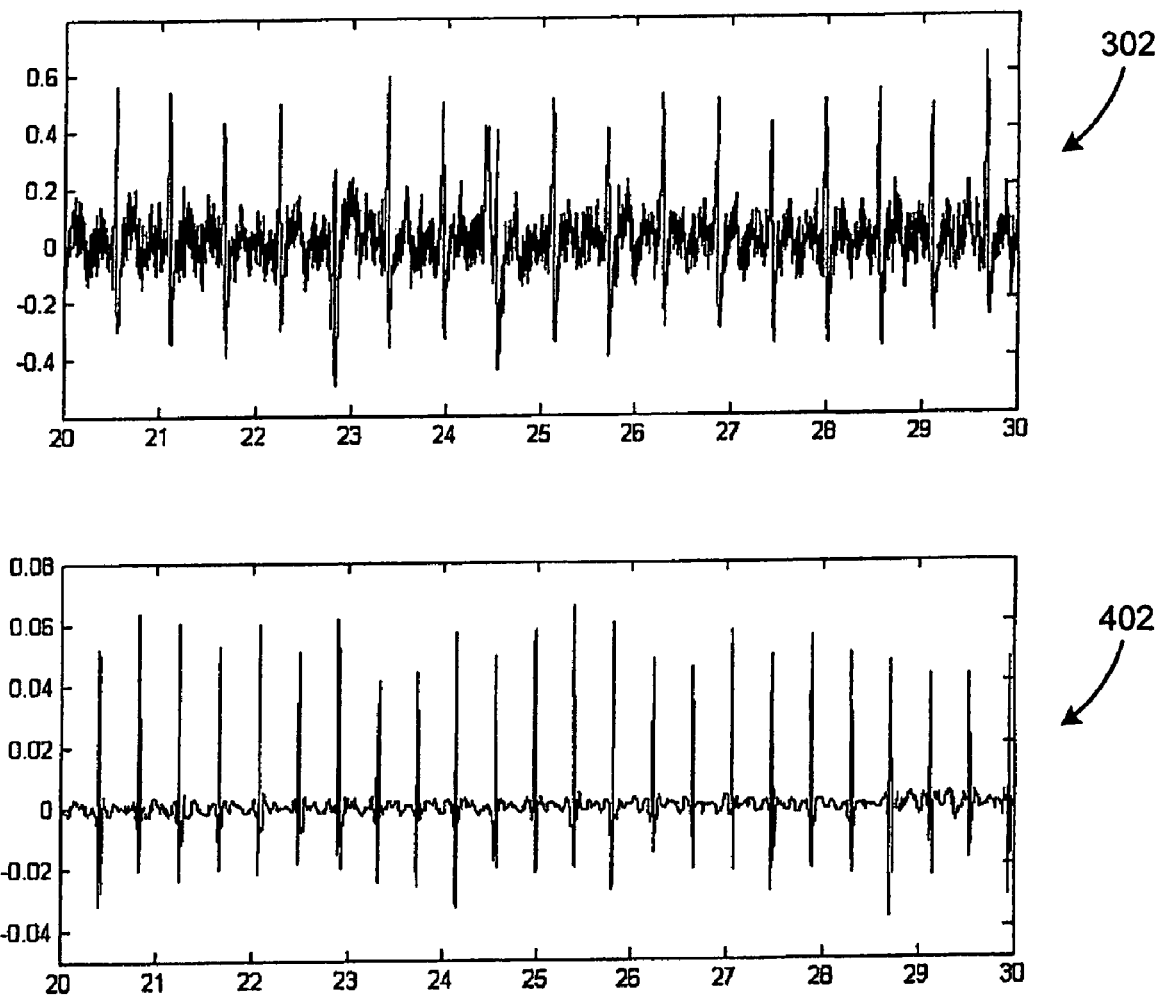
FIG. 14 is similar to FIG. 13 and shows the time of 20 to 30 seconds, for patient A.
Figure 15:
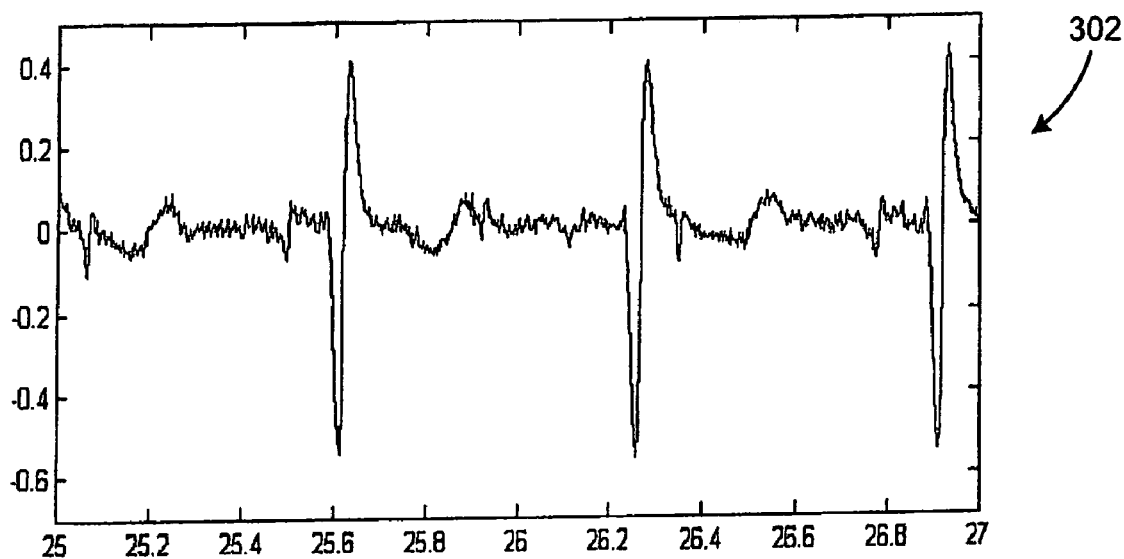
FIG. 15 is similar to FIG. 13 and shows the time of 25 to 27 seconds, for patient B.
Figure 15:
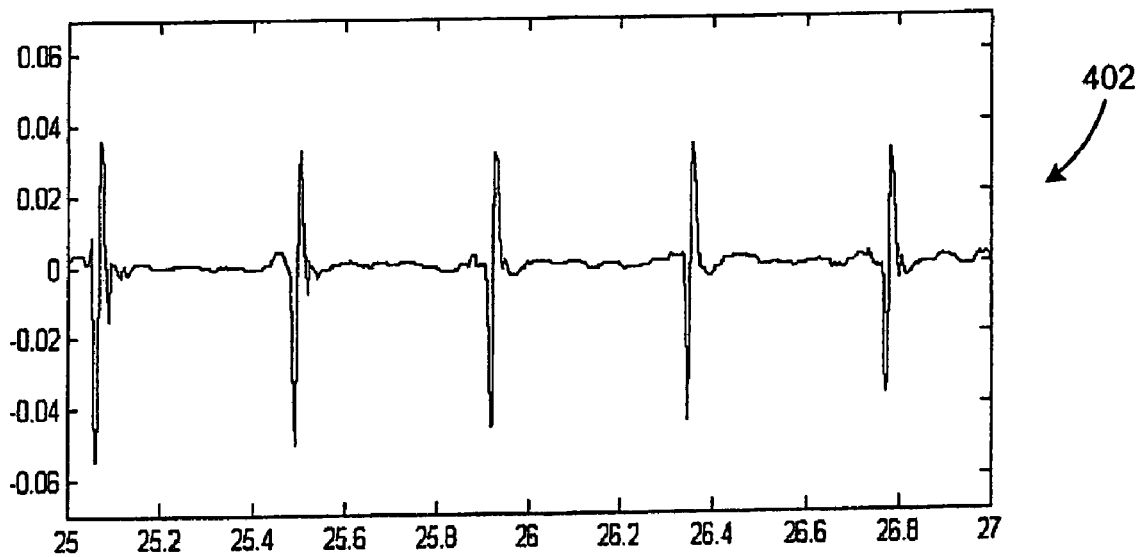
Figure 16:
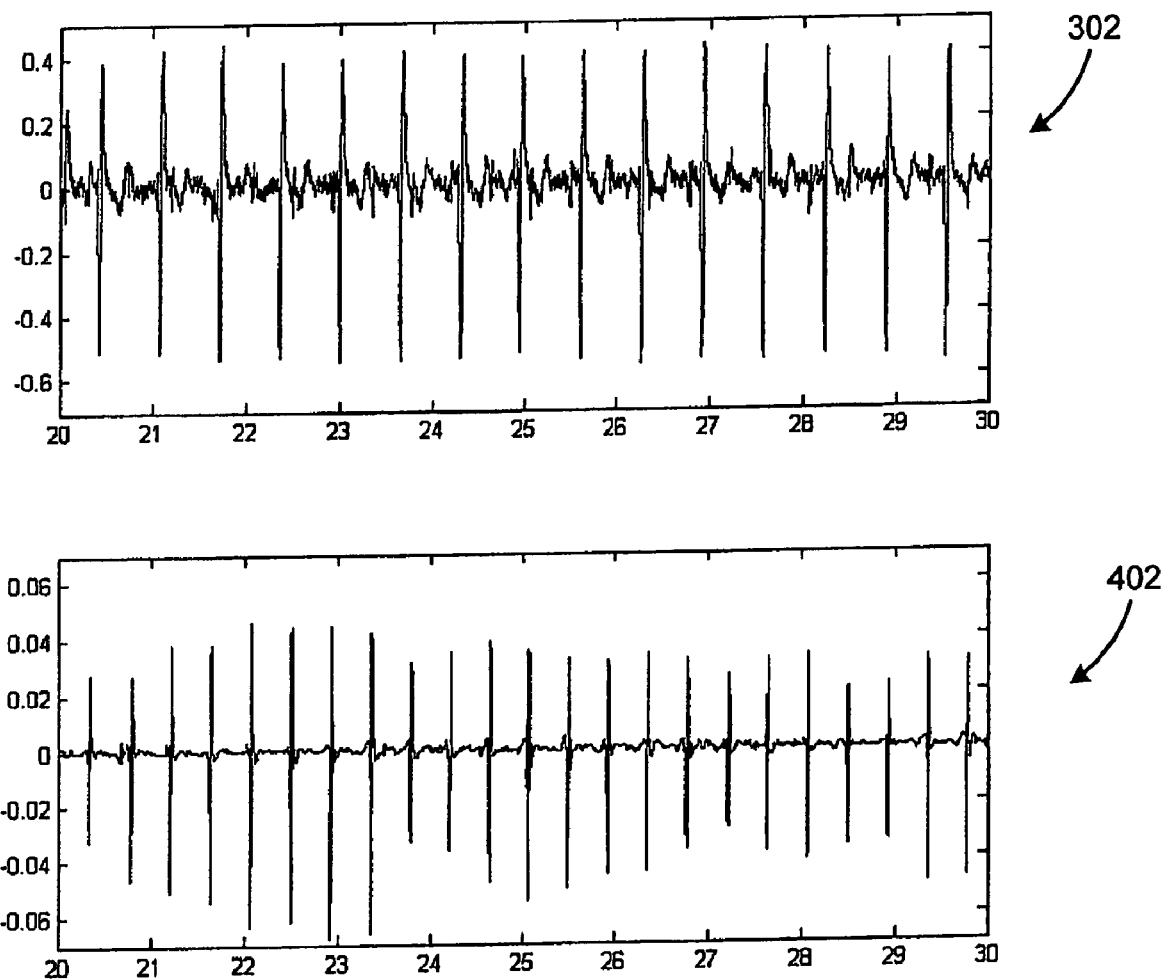
FIG. 16 is similar to FIG. 13 and shows the time of 20 to 30 seconds, for patient B.

FIG. 13 shows the raw abdominal ECG and corresponding extracted fECG for the 21st week of gestation at the time of 0 to 2 seconds, for patient A. FIG. 14 shows the time of 20 to 30 seconds. FIG. 15 shows the time of 25 to 27 seconds, for patient B. FIG. 16 shows the time of 20 to 30 seconds. FIG. 17 shows the time of 9 to 11 seconds, for patient C. FIG. 18 shows the time of 0 to 10 seconds.

FIG. 19 shows the raw abdominal ECG and corresponding extracted fECG for the 24th week of gestation at the time of 18 to 20 seconds. FIG. 20 shows the time of 0 to 10 seconds.

Subsequently, PR, QT, QTc and QRS durations were computed for these gestation weeks (via curve fitting of the retrieved fECG when P or T components were found), as indicated in exemplary TABLE 1.

TABLE 1

PR, QT, QTc and QRS Durations

| Week of Gestation | PR (millisec) | QT (msec) | QTc (msec) Bazett equation | QRS (msec) |
|---|---|---|---|---|
| 20 | 95 | 258 | 395 | 35 |
| 21-A | 104 | 279 | 436 | 38 |
| 21-B | 103 | 285 | 437 | 40.5 |
| 21-C | 112 | 262 | 419 | 32 |
| 24 | 104 | 276 | 437 | 38 |
| 28 | 112 | 269 | 420 | 41.5 |

These are well within ranges of the above durations for the corresponding heart-rates. QTc was computed by Bazett's equation, as will be appreciated by those skilled in the art. In TABLE 1, PR and QT durations are based on curve-fitting inside the S-Q interval of the extracted fECG. Values given are averages per each patient, when P or Q components were detectable (as computed over the first 100-150 beats in each data set). Exemplary discussion of the ECG signal is presented herein in connection with FIG. 21.

Evaluation of fECG is expected to have significance in diagnosing and monitoring treatment of fetal arrhythmias. It is expected to have influence in choosing safe and potentially effective medication for an individual fetus. Beat-to-beat fECG can be retrieved on-line (automatically and without averaging) from surface maternal electrodes as early as 20 weeks gestational age, as described herein.

Figure 21:
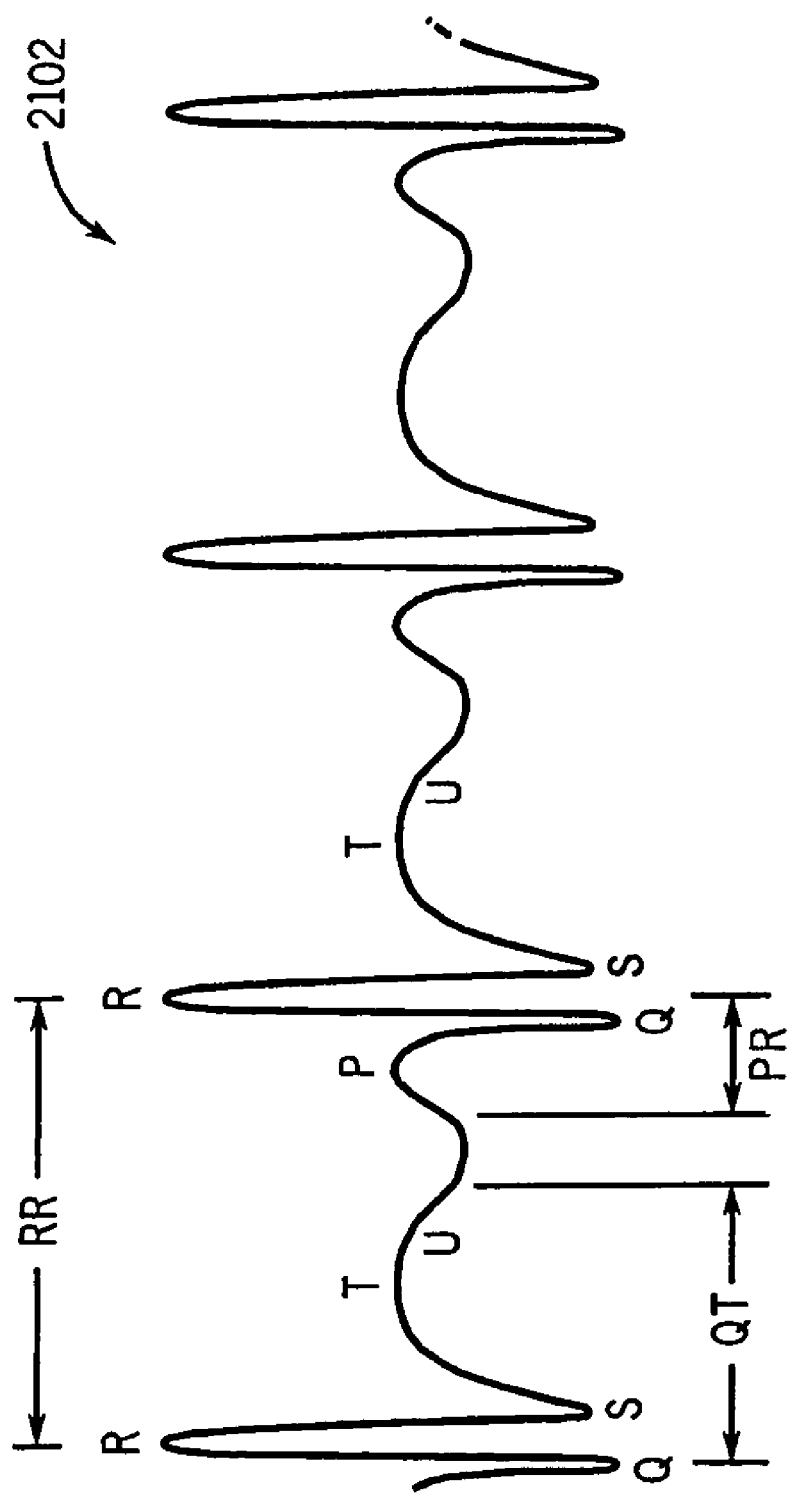
FIG. 21 represents a prior art ECG tracing of a normal heartbeat.

Turning to FIG. 21, ECG signal 2102 represents a prior art ECG tracing of a normal heartbeat. The ECG signal 210 comprises a P wave, a QRS complex, and a T wave. A small U wave is not normally visible. The P wave comprises an electrical signature of the current that causes atrial contraction. Both the left and right atria contract simultaneously. The relationship of the P wave to QRS complexes determines the presence of a heart block. Irregular or absent P waves may indicate arrhythmia. The shape of the P waves may indicate atrial problems.

The QRS complex corresponds to the current that causes contraction of the left and right ventricles, which is much more forceful than that of the atria and involves more muscle mass, thus resulting in a greater ECG deflection. The Q wave, when present, represents the small horizontal (left to right) current as the action potential travels through the interventricular septum. Very wide and deep Q waves do not have a septal origin, but indicate myocardial infarction that involves the full depth of the myocardium and has left a scar. The R and S waves indicate contraction of the myocardium itself. Abnormalities in the QRS complex may indicate bundle branch block (when wide), ventricular origin of tachycardia, ventricular hypertrophy or other ventricular abnormalities. The complexes are often small in pericarditis or pericardial effusion. The T wave represents the repolarization of the ventricles. The ST segment connects the QRS complex and the T wave.

The QT interval is measured from the beginning of the QRS complex to the end of the T wave. The QT interval as well as the corrected QT interval are important in the diagnosis of long QT syndrome and short QT syndrome. The QT interval varies based on the heart rate, and various correction factors have been developed to correct the QT interval for the heart rate. The PR interval is measured from the P wave to the QRS complex.

Figure 22:
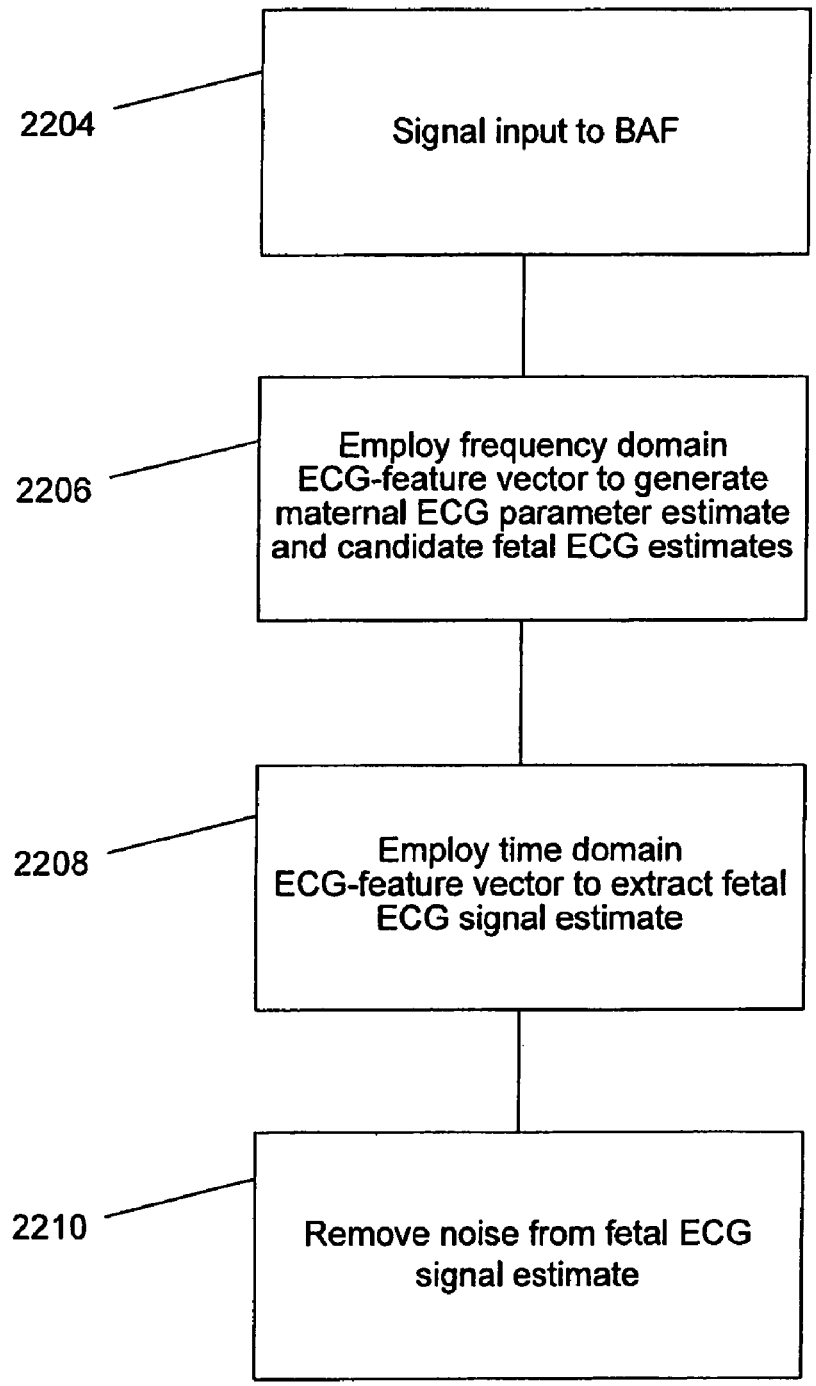
FIG. 22 is a representation of an exemplary logic flow for an implementation of the apparatus of FIG. 1.

An illustrative description of an exemplary operation of an implementation of the apparatus 100 is presented, for explanatory purposes. Turning to FIG. 22, in exemplary logic flow 2202 at Step 2204, a signal is input into a first blind adaptive filter stage and the signal comprises maternal electrocardiogram information, fetal electrocardiogram information, and non-electrocardiogram noise. At Step 2206, a feature vector of basic frequency domain features that are common to electrocardiogram signals is employed at the first blind adaptive filter stage to generate a maternal electrocardiogram parameter estimate and a set of candidate fetal electrocardiogram estimates that satisfy the feature vector of basic frequency domain features. The maternal electrocardiogram parameter estimate satisfies the feature vector of basic frequency domain features. The set of candidate fetal electrocardiogram estimates satisfies the feature vector of basic frequency domain features. The maternal electrocardiogram parameter estimate and the set of candidate fetal electrocardiogram estimates are input into a second blind adaptive filter stage. At Step 2208, a feature vector of basic time domain features that are common to electrocardiogram signals is employed at the second blind adaptive filter stage to extract an initial fetal electrocardiogram signal estimate that satisfies the feature vector of basic time domain features. At Step 2210, one or more sets of selected time samples and/or segments of the initial fetal electrocardiogram signal estimate are filtered to remove noise from the initial fetal electrocardiogram signal estimate to yield a final fetal electrocardiogram signal estimate.

A blind adaptive filter of the apparatus 100 in an example employs a frequency domain ECG-feature vector and a time domain ECG feature vector with a maternal ECG parameter estimate and a set of candidate fetal ECG estimates that satisfy the frequency domain ECG-feature-vector, to extract a fetal ECG signal estimate from raw abdominal ECG signals of a pregnant female. The fetal ECG signal estimate satisfies the frequency domain ECG feature-vector and the time domain ECG feature vector. The maternal ECG parameter estimate satisfies the frequency domain ECG-feature-vector. The set of candidate fetal ECG estimates satisfies the frequency domain ECG-feature-vector.

The frequency domain ECG-feature vector comprises a feature vector of basic frequency domain features that are common to ECG signals. The time domain ECG feature vector comprises a feature vector of basic time domain features that are common to ECG signals. The blind adaptive filter employs the frequency domain ECG-feature vector to extract the set of candidate fetal ECG estimates that satisfy the frequency domain ECG-feature-vector. The blind adaptive filter employs the time domain ECG feature vector with input, of the maternal ECG parameter estimate and the set of candidate fetal ECG estimates, to extract the fetal ECG signal estimate that satisfies the frequency domain ECG feature-vector and the time domain ECG feature vector.

The fetal ECG signal estimate is extracted from raw abdominal ECG signals of a pregnant female to satisfy the frequency domain ECG feature-vector and the time domain ECG feature vector through employment of the blind adaptive filter. The blind adaptive filter employs the frequency domain ECG-feature vector and the time domain ECG feature vector with the maternal ECG parameter estimate and the set of candidate fetal ECG estimates that satisfy the frequency domain ECG-feature-vector.

The blind adaptive filter comprises a second blind adaptive filter stage. The fetal ECG signal estimate that satisfies the time domain ECG feature vector comprises an initial fetal ECG signal estimate that satisfies the time domain ECG feature vector. A first blind adaptive filter stage of the apparatus 100 employs the frequency domain ECG-feature vector with an input signal that comprises maternal ECG information, fetal ECG information, and non ECG noise to generate the maternal ECG parameter estimate and the set of candidate fetal ECG estimates that satisfy the frequency domain ECG-feature vector. The second blind adaptive filter stage employs the time domain ECG feature vector with the maternal ECG parameter estimate and the set of candidate fetal ECG estimates from the first blind adaptive filter stage to extract the initial fetal ECG signal estimate that satisfies the time domain ECG feature vector. The second blind adaptive filter stage filters one or more sets of selected time samples and/or segments of the initial fetal ECG signal estimate to remove noise from the initial fetal ECG signal estimate to yield a final fetal ECG signal estimate.

There is employed at the blind adaptive filter a time domain ECG feature vector with the maternal ECG parameter estimate and the set of candidate fetal ECG estimates to extract the fetal ECG signal estimate as an initial fetal ECG signal estimate that satisfies the time domain ECG feature vector. There is filtered at the blind adaptive filter one or more sets of selected time samples and/or segments of the initial fetal ECG signal estimate to remove noise from the initial fetal ECG signal estimate to yield a final fetal ECG signal estimate.

The blind adaptive filter comprises a neural network that determines a particular harmonic filter band whose output minimizes a distance between: 1) a time-domain feature of the set of candidate fetal ECG estimates in terms of higher absolute amplitude of a narrow time interval around the R wave and lower absolute value amplitudes of a wider time interval over the T, U, and P parts; and 2) outputs of a set of harmonic band-pass filters that provides the maternal ECG parameter estimate and the set of candidate fetal ECG estimates.

There is determined a particular harmonic filter band whose output minimizes a distance between: 1) a time-domain feature of the set of candidate fetal ECG estimates in terms of higher absolute amplitude of a narrow time interval around the R wave and lower absolute value amplitudes of a wider time interval over the T, U, and P parts; and 2) outputs of a set of harmonic band-pass filters that provides the maternal ECG parameter estimate and the set of candidate fetal ECG estimates.

The blind adaptive filter correlates: 1) each of the outputs of a set of harmonic band-pass filters that provides the maternal ECG parameter estimate and the set of candidate fetal ECG estimates; and 2) an output of a narrow band-pass filter when compressed by a factor of a ratio of a base frequency of the set of harmonic band-pass filters and an inverse of duration of raw input to the set of harmonic band-pass filters.

There are correlated: 1) each of the outputs of a set of harmonic band-pass filters that provides the maternal ECG parameter estimate and the set of candidate fetal ECG estimates; and 2) an output of a narrow band-pass filter when compressed by a factor of a ratio of a base frequency of the set of harmonic band-pass filters and an inverse of duration of raw input to the set of harmonic band-pass filters.

A display of the apparatus 100 presents a trace of the fetal ECG signal estimate versus time. The display presents PR and QT parts, derived from durations of the fetal ECG signal estimate, for selected fetal ECG samples and/or segments of the trace of the fetal ECG signal estimate versus time. The display presents average durations of PR and QT parts over a plurality of samples of the PR and QT parts.

The fetal ECG signal estimate is displayed versus time. PR and QT parts are derived from durations of the fetal ECG signal estimate. The PR and QT parts are displayed for selected fetal ECG samples and/or segments of the fetal ECG signal estimate versus time. Average durations of PR and QT parts over a plurality of samples of the PR and QT parts are displayed.

The blind adaptive filter automatically and without human interaction employs the frequency domain ECG-feature vector and the time domain ECG feature vector with the maternal ECG parameter estimate and the set of candidate fetal ECG estimates that satisfy the frequency domain ECG-feature-vector, to automatically and without human interaction extract the fetal ECG signal estimate from the raw abdominal ECG signals of the pregnant female.

There is employed automatically and without human interaction at the blind adaptive filter a feature vector of basic frequency domain features that are common to ECG signals to extract the set of candidate fetal ECG estimates that satisfy the frequency domain vector. There is employed automatically and without human interaction at the blind adaptive filter a feature vector of basic time domain features that are common to ECG signals with input, of the maternal ECG parameter estimate and the set of candidate fetal ECG estimates, to extract the fetal ECG signal estimate with satisfaction of the feature vector of basic frequency domain features that are common to ECG signals and the feature vector of basic time domain features that are common to ECG signals.

A fetal ECG signal estimate that satisfies a time domain vector is extracted through employment of a blind adaptive filter that employs the time domain vector with a maternal ECG parameter estimate and a set of candidate fetal ECG estimates that satisfy a frequency domain vector. The maternal ECG parameter estimate satisfies the frequency domain vector. The set of candidate fetal ECG estimates satisfies the frequency domain vector.

There is extracted at least as early as week twenty of gestation the fetal ECG signal estimate that satisfies the time domain vector through employment of the blind adaptive filter that employs the time domain vector with the maternal ECG parameter estimate and the set of candidate fetal ECG estimates that satisfy the frequency domain vector.

An implementation encompasses an article. The article comprises one or more computer-readable signal-bearing media. The article comprises means in the one or more media for extracting a fetal ECG signal estimate that satisfies a time domain vector through employment of a blind adaptive filter that employs the time domain vector with a maternal ECG parameter estimate and a set of candidate fetal ECG estimates that satisfy a frequency domain vector. The maternal ECG parameter estimate satisfies the frequency domain vector. The set of candidate fetal ECG estimates satisfies the frequency domain vector.

The means in the one or more media for extracting a fetal ECG signal estimate that satisfies a time domain vector through employment of a blind adaptive filter that employs the time domain vector with a maternal ECG parameter estimate and a set of candidate fetal ECG estimates that satisfy a frequency domain vector comprises means in the one or more media for extracting at least as early as week twenty of gestation the fetal ECG signal estimate that satisfies the time domain vector through employment of the blind adaptive filter that employs the time domain vector with the maternal ECG parameter estimate and the set of candidate fetal ECG estimates that satisfy the frequency domain vector. The maternal electrocardiogram parameter estimate satisfies the feature vector of basic frequency domain features. The set of candidate fetal electrocardiogram estimates satisfies the feature vector of basic frequency domain features.

An implementation encompasses an article. The article comprises one or more computer-readable signal-bearing media. The article comprises means in the one or more media for inputting a signal that comprises maternal electrocardiogram information, fetal electrocardiogram information, and non-electrocardiogram noise into a first blind adaptive filter stage. The article comprises means in the one or more media for employing a feature vector of basic frequency domain features that are common to electrocardiogram signals at the first blind adaptive filter stage to generate a maternal electrocardiogram parameter estimate and a set of candidate fetal electrocardiogram estimates that satisfy the feature vector of basic frequency domain features. The article comprises means in the one or more media for inputting the maternal electrocardiogram parameter estimate and the set of candidate fetal electrocardiogram estimates into a second blind adaptive filter stage. The article comprises means in the one or more media for employing a feature vector of basic time domain features that are common to electrocardiogram signals at the second blind adaptive filter stage to extract an initial fetal electrocardiogram signal estimate that satisfies the feature vector of basic time domain features. The article comprises means in the one or more media for filtering one or more sets of selected time samples and/or segments of the initial fetal electrocardiogram signal estimate to remove noise from the initial fetal electrocardiogram signal estimate to yield a final fetal electrocardiogram signal estimate.

In the exemplary studies discussed herein, all examples were automatically executed on real-patient digitized raw abdominal data, without any human interaction, visual or otherwise.

An implementation of the apparatus 100 in an example comprises a plurality of components such as one or more of electronic components, hardware components, and/or computer software components. A number of such components can be combined or divided in an implementation of the apparatus 100. An exemplary component of an implementation of the apparatus 100 employs and/or comprises a set and/or series of computer instructions written in or implemented with any of a number of programming languages, as will be appreciated by those skilled in the art. An implementation of the apparatus 100 in an example comprises any (e.g., horizontal, oblique, or vertical) orientation, with the description and figures herein illustrating an exemplary orientation of an implementation of the apparatus 100, for explanatory purposes.

An implementation of the apparatus 100 in an example employs one or more computer readable signal bearing media. A computer-readable signal-bearing medium in an example stores software, firmware and/or assembly language for performing one or more portions of one or more implementations. An example of a computer-readable signal bearing medium for an implementation of the apparatus 100 comprises the recordable data storage medium of the memory 104. A computer-readable signal-bearing medium for an implementation of the apparatus 100 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer readable signal-bearing medium comprises a modulated carrier signal transmitted over a network comprising or coupled with an implementation of the apparatus 100, for instance, one or more of a telephone network, a local area network ("LAN"), a wide area network ("WAN"), the Internet, and/or a wireless network.

The steps or operations described herein are examples. There may be variations to these steps or operations without departing from the spirit of the invention. For example, the steps may be performed in a differing order, or steps may be added, deleted, or modified.

Although exemplary implementation of the invention has been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An apparatus, comprising:
   a blind adaptive filter that employs a frequency domain ECG-feature vector and a time domain ECG feature vector with a maternal ECG parameter estimate and a set of candidate fetal ECG estimates that satisfy the frequency domain ECG-feature-vector, to extract a fetal ECG signal estimate from raw abdominal ECG signals of a pregnant female, wherein the fetal ECG signal estimate satisfies the frequency domain ECG feature-vector and the time domain ECG feature vector.

2. The apparatus of claim 1, wherein the frequency domain ECG-feature vector comprises a feature vector of basic frequency domain features that are common to ECG signals, wherein the time domain ECG feature vector comprises a feature vector of basic time domain features that are common to ECG signals;
wherein the blind adaptive filter employs the frequency domain ECG-feature vector to extract the set of candidate fetal ECG estimates that satisfy the frequency domain ECG-feature-vector;
wherein the blind adaptive filter employs the time domain ECG feature vector with input, of the maternal ECG parameter estimate and the set of candidate fetal ECG estimates, to extract the fetal ECG signal estimate that satisfies the frequency domain ECG feature-vector and the time domain ECG feature vector.

3. The apparatus of claim 1, wherein the blind adaptive filter comprises a second blind adaptive filter stage, wherein the frequency domain ECG-feature vector comprises a feature vector of basic frequency domain features that are common to ECG signals, wherein the time domain ECG feature vector comprises a feature vector of basic time domain features that are common to ECG signals, wherein the fetal ECG signal estimate that satisfies the time domain ECG feature vector comprises an initial fetal ECG signal estimate that satisfies the time domain ECG feature vector, the apparatus further comprising:
a first blind adaptive filter stage that employs the frequency domain ECG-feature vector with an input signal that comprises maternal ECG information, fetal ECG information, and non ECG noise to generate the maternal ECG parameter estimate and the set of candidate fetal ECG estimates that satisfy the frequency domain ECG-feature vector;
wherein the second blind adaptive filter stage employs the time domain ECG feature vector with the maternal ECG parameter estimate and the set of candidate fetal ECG estimates from the first blind adaptive filter stage to extract the initial fetal ECG signal estimate that satisfies the time domain ECG feature vector;
wherein the second blind adaptive filter stage filters one or more sets of selected time segments of the initial fetal ECG signal estimate to remove noise from the initial fetal ECG signal estimate to yield a final fetal ECG signal estimate.

4. The apparatus of claim 1, wherein;
wherein the blind adaptive filter comprises a neural network that determines a particular harmonic filter band whose output minimizes a distance between:
a time-domain feature of the set of candidate fetal ECG estimates in terms of higher absolute amplitude of a narrow time interval around the R wave and lower absolute value amplitudes of a wider time interval over the T, U, and P parts; and
outputs of a set of harmonic band-pass filters that provides the maternal ECG parameter estimate and the set of candidate fetal ECG estimates.

5. The apparatus of claim 1, wherein the blind adaptive filter correlates:
each of the outputs of a set of harmonic band-pass filters that provides the maternal ECG parameter estimate and the set of candidate fetal ECG estimates; and
an output of a narrow band-pass filter when compressed by a factor of a ratio of a base frequency of the set of harmonic band-pass filters and an inverse of duration of raw input to the set of harmonic band-pass filters.

6. The apparatus of claim 1, further comprising:
a display that presents a trace of the fetal ECG signal estimate versus time.

7. The apparatus of claim 6, wherein the display presents PR and QT parts, derived from durations of the fetal ECG signal estimate, for selected fetal ECG segments of the trace of the fetal ECG signal estimate versus time.

8. The apparatus of claim 6, wherein the display presents average durations of PR and QT parts over a plurality of samples of the PR and QT parts.

9. The apparatus of claim 1, wherein the blind adaptive filter automatically and without human interaction employs the frequency domain ECG-feature vector and the time domain ECG feature vector with the maternal ECG parameter estimate and the set of candidate fetal ECG estimates that satisfy the frequency domain ECG-feature-vector, to automatically and without human interaction extract the fetal ECG signal estimate from the raw abdominal ECG signals of the pregnant female.

10. A method, comprising the step of:
extracting a fetal ECG signal estimate that satisfies a frequency domain vector and a time domain vector through employment of a blind adaptive filter that employs the time domain vector with a maternal ECG parameter estimate and a set of candidate fetal ECG estimates that satisfy the frequency domain vector.

11. The method of claim 10, wherein the step of extracting the fetal ECG signal estimate that satisfies the frequency domain vector and the time domain vector through employment of the blind adaptive filter that employs the time domain vector with the maternal ECG parameter estimate and the set of candidate fetal ECG estimates that satisfy the frequency domain vector comprises the step of:
extracting at least as early as week twenty of gestation the fetal ECG signal estimate that satisfies the frequency domain vector and the time domain vector through employment of the blind adaptive filter that employs the time domain vector with the maternal ECG parameter estimate and the set of candidate fetal ECG estimates that satisfy the frequency domain vector.

12. The method of claim 10, wherein the frequency domain vector comprises a frequency domain ECG feature-vector, wherein the time domain vector comprises a time domain ECG feature vector, wherein the step of extracting the fetal ECG signal estimate that satisfies the frequency domain vector and the time domain vector through employment of the blind adaptive filter that employs the time domain vector with the maternal ECG parameter estimate and the set of candidate fetal ECG estimates that satisfy the frequency domain vector comprises the step of:
extracting the fetal ECG signal estimate from raw abdominal ECG signals of a pregnant female to satisfy the frequency domain ECG feature-vector and the time domain ECG feature vector through employment of the blind adaptive filter, wherein the blind adaptive filter employs the frequency domain ECG-feature vector and the time domain ECG feature vector with the maternal ECG parameter estimate and the set of candidate fetal ECG estimates that satisfy the frequency domain ECG-feature-vector.

13. The method of claim 10, wherein the step of extracting the fetal ECG signal estimate that satisfies the frequency domain vector and the time domain vector through employment of the blind adaptive filter that employs the time domain vector with the maternal ECG parameter estimate and the set of candidate fetal ECG estimates that satisfy the frequency domain vector comprises the steps of:

employing automatically and without human interaction at the blind adaptive filter a feature vector of basic frequency domain features that are common to ECG signals to extract the set of candidate fetal ECG estimates that satisfy the frequency domain vector; and employing automatically and without human interaction at the blind adaptive filter a feature vector of basic time domain features that are common to ECG signals with input, of the maternal ECG parameter estimate and the set of candidate fetal ECG estimates, to extract the fetal ECG signal estimate with satisfaction of the feature vector of basic frequency domain features that are common to ECG signals and the feature vector of basic time domain features that are common to ECG signals.

14. The method of claim 10, wherein the step of extracting the fetal ECU signal estimate that satisfies the frequency domain vector and the time domain vector through employment of the blind adaptive filter that employs the time domain vector with the maternal ECG parameter estimate and the set of candidate fetal ECG estimates that satisfy the frequency domain vector comprises the steps of:

employing at the blind adaptive filter a time domain ECG feature vector with the maternal ECG parameter estimate and the set of candidate fetal ECG estimates to extract the fetal ECG signal estimate as an initial fetal ECG signal estimate that satisfies the time domain ECG feature vector; and filtering at the blind adaptive filter one or more sets of selected time segments of the initial fetal ECG signal estimate to remove noise from the initial fetal ECG signal estimate to yield a final fetal ECG signal estimate.

15. The method of claim 10, wherein the step of extracting the fetal ECG signal estimate that satisfies the frequency domain vector and the time domain vector through employment of the blind adaptive filter that employs the time domain vector with the maternal ECG parameter estimate and the set of candidate fetal ECG estimates that satisfy the frequency domain vector comprises the step of:

determining a particular harmonic filter band whose output minimizes a distance between:

a time-domain feature of the set of candidate fetal ECG estimates in terms of higher absolute amplitude of a narrow time interval around the R wave and lower absolute value amplitudes of a wider time interval over the T, U, and P parts; and outputs of a set of harmonic band-pass filters that provides the maternal ECG parameter estimate and the set of candidate fetal ECG estimates.

16. The method of claim 10, wherein the step of extracting the fetal ECG signal estimate that satisfies the frequency domain vector and the time domain vector through employment of the blind adaptive filter that employs the time domain vector with the maternal ECG parameter estimate and the set of candidate fetal ECG estimates that satisfy the frequency domain vector comprises the step of:

correlating:

each of the outputs of a set of harmonic band-pass filters that provides the maternal ECG parameter estimate and the set of candidate fetal ECG estimates; and an output of a narrow band-pass filter when compressed by a factor of a ratio of a base frequency of the set of harmonic band-pass filters and an inverse of duration of raw input to the set of harmonic band-pass filters.

17. The method of claim 10, further comprising the step of:
displaying the fetal ECG signal estimate versus time.

18. The method of claim 17, further comprising the steps of:

deriving PR and QT parts from durations of the fetal ECG signal estimate; and displaying the PR and QT parts for selected fetal ECG segments of the fetal ECG signal estimate versus time.

19. The method of claim 17, further comprising the step of:
displaying average durations of PR and QT parts over a plurality of samples of the PR and QT parts.

20. A method, comprising the steps of:

inputting a signal that comprises maternal electrocardiogram information, fetal electrocardiogram information, and non-electrocardiogram noise into a first blind adaptive filter stage;

employing a feature vector of basic frequency domain features that are common to electrocardiogram signals at the first blind adaptive filter stage to generate a maternal electrocardiogram parameter estimate and a set of candidate fetal electrocardiogram estimates that satisfy the feature vector of basic frequency domain features;

inputting the maternal electrocardiogram parameter estimate and the set of candidate fetal electrocardiogram estimates into a second blind adaptive filter stage;

employing a feature vector of basic time domain features that are common to electrocardiogram signals at the second blind adaptive filter stage to extract an initial fetal electrocardiogram signal estimate that satisfies the feature vector of basic time domain features; and filtering one or more sets of selected time samples of the initial fetal electrocardiogram signal estimate to remove noise from the initial fetal electrocardiogram signal estimate to yield a final fetal electrocardiogram signal estimate.

* * * * *